(12) United States Patent
Bastian et al.

(10) Patent No.: US 8,507,490 B2
(45) Date of Patent: Aug. 13, 2013

(54) TETRASUBSTITUTED PYRIDAZINE HEDGEHOG PATHWAY ANTAGONISTS

(75) Inventors: Jolie Anne Bastian, Indianapolis, IN (US); Julia Marie Clay, Zionsville, IN (US); Jeffrey Daniel Cohen, Indianapolis, IN (US); Philip Arthur Hipskind, New Palestine, IN (US); Karen Lynn Lobb, Indianaplois, IN (US); Daniel Jon Sall, Greenwood, IN (US); Michelle Lee Thompson, Greenwood, IN (US); Takako Wilson (nee Takakuwa), Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 9 days.

(21) Appl. No.: 13/122,216

(22) PCT Filed: Nov. 5, 2009

(86) PCT No.: PCT/US2009/063370
§ 371 (c)(1),
(2), (4) Date: Apr. 1, 2011

(87) PCT Pub. No.: WO2010/056588
PCT Pub. Date: May 20, 2010

(65) Prior Publication Data
US 2011/0263602 A1    Oct. 27, 2011

Related U.S. Application Data

(60) Provisional application No. 61/115,332, filed on Nov. 17, 2008.

(51) Int. Cl.
*C07D 401/14* (2006.01)
*A61K 31/501* (2006.01)
*A61P 35/00* (2006.01)

(52) U.S. Cl.
USPC ..................................... 514/252.03; 544/238

(58) Field of Classification Search
USPC ..................................... 514/252.03; 544/238
See application file for complete search history.

(56) References Cited

U.S. PATENT DOCUMENTS

| | | | |
|---|---|---|---|
| 3,753,988 A | 8/1973 | Rodway et al. | |
| 5,985,878 A | 11/1999 | Stokbroekx et al. | |
| 6,432,970 B2 | 8/2002 | Beachy et al. | |
| 2009/0048259 A1 | 2/2009 | Austin et al. | |
| 2010/0324048 A1 | 12/2010 | Hipskind | |
| 2011/0046143 A1 | 2/2011 | Hipskind | |

FOREIGN PATENT DOCUMENTS

| WO | WO 97/26258 A1 | 7/1997 |
|---|---|---|
| WO | WO 99/52534 A1 | 10/1999 |
| WO | WO 00/74706 A1 | 12/2000 |
| WO | WO 03/088970 A2 | 10/2003 |
| WO | WO 2004/020599 A2 | 3/2004 |
| WO | 2005/033288 A2 | 4/2005 |
| WO | WO 2005/080378 A1 | 9/2005 |

(Continued)

OTHER PUBLICATIONS

Merchant, et al., Clin. Cancer Res., 16(12), Jun. 15, 2010.*

(Continued)

*Primary Examiner* — Susanna Moore
*Assistant Examiner* — Cecilia M Jaisle
(74) *Attorney, Agent, or Firm* — Danica Hostettler; John C. Demeter

(57) ABSTRACT

The present invention provides novel tetrasubstituted pyridine hedgehog pathway antagonists of the following formula I (I) or a pharmaceutically acceptable salt thereof, wherein: X is C—$R^1$ or N; $R^1$ is hydrogen, fluoro or cyano; $R^2$ is formula II (II), piperidinyl, or gem di-F-substituted cyclohexyl; $R^3$ is methyl or trifluoromethyl; $R^4$ is pyrrolidinyl, morpholinyl or pyridyl, amino or dimethylamino; $R^5$ is trifluoromethyl or methylsulfonyl; $R^6$ is hydrogen or methyl; and $R^7$, $R^8$, $R^9$, $R^{10}$ and $R^{11}$ are independently hydrogen fluoro, cyano, chloro, methyl, trifluoromethyl, trifluoromethoxy or methylsulfonyl, provided that at least two of $R^7$, $R^8$, $R^9$, $R^{10}$ and $R^{11}$ are hydrogen useful in the treatment of cancer.

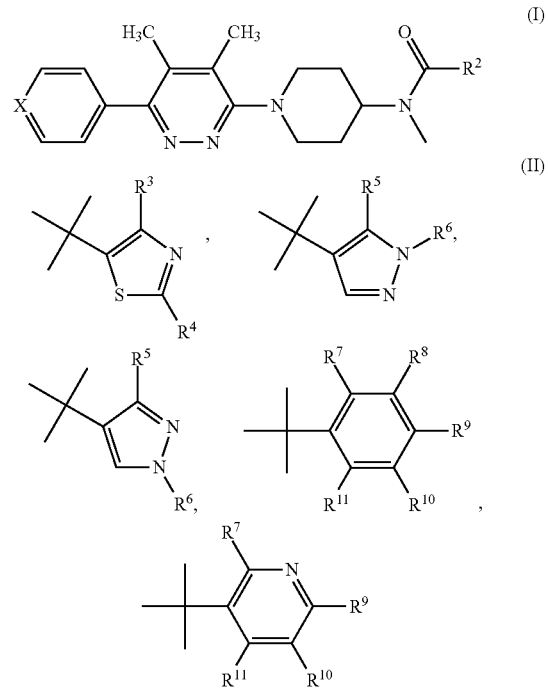

15 Claims, No Drawings

(56) References Cited

FOREIGN PATENT DOCUMENTS

| WO | WO 2006/004589 A2 | 1/2006 |
|---|---|---|
| WO | WO 2006/028958 A2 | 3/2006 |
| WO | WO 2008/028689 A1 | 3/2008 |
| WO | WO 2008/110611 A1 | 9/2008 |
| WO | WO 2009/002469 A1 | 12/2008 |
| WO | WO 2009/035568 A1 | 3/2009 |
| WO | WO 2009/134574 A2 | 11/2009 |
| WO | WO 2010/007120 A1 | 1/2010 |
| WO | WO 2010/056620 A1 | 5/2010 |
| WO | WO 2010/062507 A1 | 6/2010 |

OTHER PUBLICATIONS

Scales, et al., Trends in Pharmacological Sciences, 30, 8, 2009, 303-312.*

Lin, et al., PLoS ONE, Dec. 2010, 5, 12, e15262.*

Frank-Kamenetsky, M., et al., "Small-molecular modulators of Hedgehog signaling: identification and characterization of Smoothened agonists and antagonists," Journal of Biolology vol. 1, Issue 2, Article 10, pp. 10.1-10.19 (2002).

Lee, J., et al., "A small-muleclar antagonist of the Hedgehog signaling pathway," ChemBioChem, vol. 8, pp. 1916-1919 (2007).

McMahon, G., VEGF Receptor Signaling in Tumor Angiogenisis. The Oncologist, 5(suppl 1):3-10 (2000). [www.TheOncologist.com].

Tremblay, M., et al., "Semisynthetic cyclopamine analogues as potent and orally bioavailable Hedgehog pathway antagonists," J. Med. Chem., vol. 51, pp. 6646-6649 (2008).

Tremblay, M., et al., "Recent patents for Hedgehog pathway inhibitors for the treatment of malignancy," Expert Opin. Ther. Patents 19(8):1039-1056 (2009).

Pinedo, et al., "Translational Research: The Role of VEGF in Tumor Angiogenesis," The Oncologist, 5(suppl 1):1-2 (2000) [www.TheOncologist.com].

* cited by examiner

TETRASUBSTITUTED PYRIDAZINE HEDGEHOG PATHWAY ANTAGONISTS

This application is a national phase application under 35 U.S.C. Section 371 of PCT/US2009/063370, filed Nov. 5, 2009, which claims the benefit under 35 U.S.C. Section 119(e) of U.S. provisional patent application 61/115,332, filed Nov. 17, 2008.

The present invention relates to Hedgehog pathway antagonists and, more specifically, to novel tetrasubstituted pyridazines and therapeutic use thereof. The Hedgehog (Hh) signaling pathway plays an important role in embryonic pattern formation and adult tissue maintenance by directing cell differentiation and proliferation. The Hedgehog (Hh) protein family, which includes Sonic Hedgehog (Shh), Indian Hedgehog (Ihh), and Desert Hedgehog (Dhh) are secreted glycoproteins that undergo post-translational modifications, including autocatalytic cleavage and coupling of cholesterol to the amino-terminal peptide to form the fragment that possesses signaling activity. Hh binds to the twelve-pass transmembrane protein Ptch (Ptch1 and Ptch2), thereby alleviating Ptch-mediated suppression of Smoothened (Smo). Smo activation triggers a series of intracellular events culminating in the stabilization of the Gli transcription factors (Gli1, Gli2, and Gli3) and the expression of Gli-dependent genes that are responsible for cell proliferation, cell survival, angiogenesis and invasion.

Hh signaling has recently attracted considerable interest based on the discovery that aberrant activation of Shh signaling leads to the formation of various tumors, e.g., pancreatic cancer, medulloblastoma, basal cell carcinoma, small cell lung cancer, and prostate cancer. Several Hh antagonists have been reported in the art, such as the steroidal alkaloid compound IP-609; the aminoproline compound CUR61414; and the 2,4-disubstituted thiazole compound JK18. WO2005033288 discloses certain 1,4-disubstituted phthalazine compounds asserted to be hedgehog antagonists. Similarly, WO2008110611 discloses certain 1,4 disubstituted phthalazine compounds related to the diagnosis and treatment of pathologies related to the hedgehog pathway.

There still exists a need for potent hedgehog pathway inhibitors, particularly those having desirable pharmacodynamic, pharmacokinetic and toxicology profiles. The present invention provides novel tetrasubstituted pyridazines that are potent antagonists of this pathway.

The present invention provides a compound of Formula I:

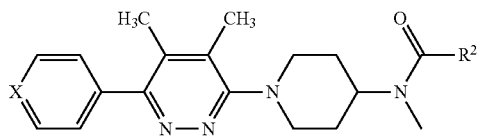

or a pharmaceutically acceptable salt thereof, wherein:

X is C—$R^1$ or N;

$R^1$ is hydrogen, fluoro or cyano;

$R^2$ is

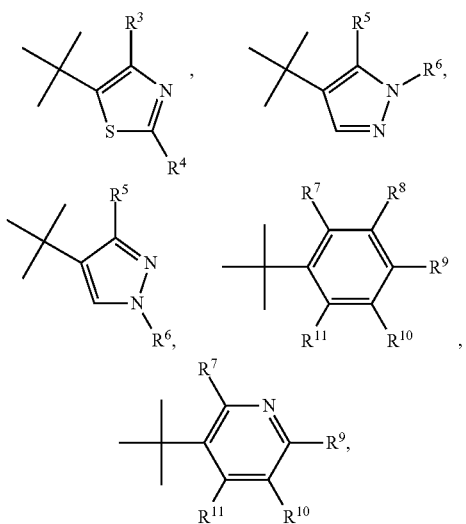

piperidinyl, or gem di-fluoro-substituted cyclohexyl;

$R^3$ is methyl or trifluoromethyl;

$R^4$ is pyrrolidinyl, morpholinyl or pyridyl, amino or dimethylamino;

$R^5$ is trifluoromethyl, or methylsulfonyl;

$R^6$ is hydrogen or methyl; and $R^7$, $R^8$, $R^9$, $R^{10}$ and $R^{11}$ are independently hydrogen fluoro, cyano, chloro, methyl, trifluoromethyl, trifluoromethoxy or methylsulfonyl, provided that at least two of $R^7$, $R^8$, $R^9$, $R^{10}$ and $R^{11}$ are hydrogen.

The cross mark ("—┼—") used in the $R^2$ substituents depicts the point of attachment for a particular $R^2$ substituent to the amide moiety within Formula I.

It will be understood by the skilled artisan that the compounds of the present invention comprise a tertiary amine moiety and are capable of reaction with a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

Specific embodiments of the invention include compounds of Formula I, or a pharmaceutically acceptable salt thereof, wherein:

(a) X is C—$R^1$ (b) $R^1$ is fluoro;

(c) $R^1$ is cyano;

(d) $R^2$ is:

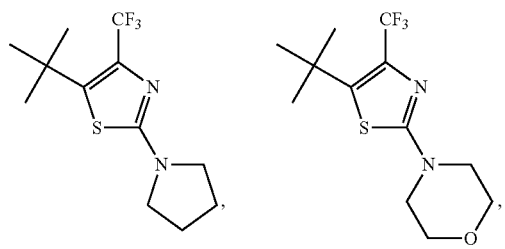

-continued

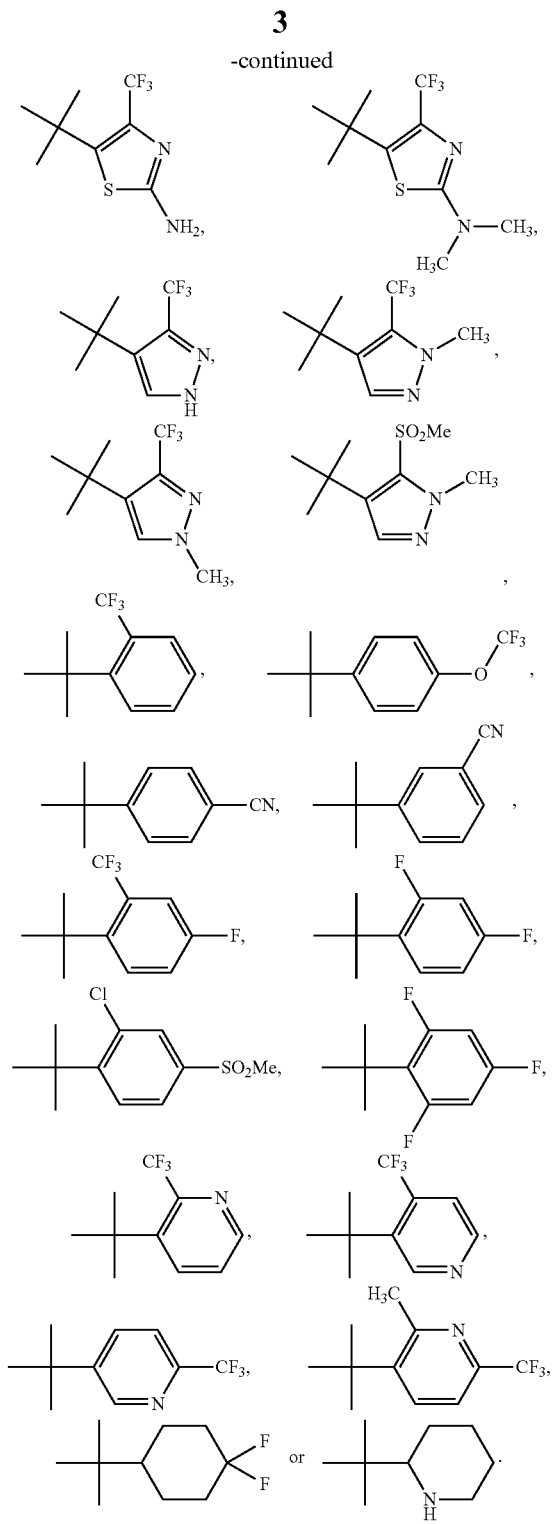

(e) $R^2$ is

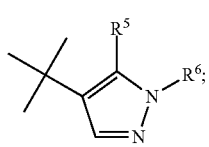

(f) $R^2$ is

[structure with CF3, t-Bu, pyrazole N-CH3]

(f) $R^2$ is

[pyridine structure with $R^7$, $R^9$, $R^{10}$, $R^{11}$ and t-Bu]

(g) $R^2$ is

[pyridine with CF3 and t-Bu]

(h) $R^1$ is fluoro and $R^2$ is

[pyrazole with $R^5$, $R^6$ and t-Bu]

(i) $R^1$ is cyano and $R^2$ is

[pyridine structure with $R^7$, $R^9$, $R^{10}$, $R^{11}$ and t-Bu]

The present invention also provides a pharmaceutical composition comprising a compound of Formula I, or a pharmaceutically acceptable salt thereof, in combination with a pharmaceutically acceptable excipient, carrier or diluent.

The compounds of the present invention are preferably formulated as pharmaceutical compositions administered by a variety of routes. Preferably, such compositions are for oral or intravenous administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995).

The present invention also provides a method of treating brain cancer, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer or melanoma in a patient comprising administering to a patient in need of such treatment an effective amount of a compound of Formula I, or a pharmaceutically acceptable salt thereof.

It will be understood that the amount of the compound actually administered will be determined by a physician under the relevant circumstances, including the condition to be treated, the chosen route of administration, the actual compound or compounds administered, the age, weight, and response of the individual patient, and the severity of the patient's symptoms. Dosages per day normally fall within the range of about 0.1 to about 5 mg/kg of body weight. In some instances dosage levels below the lower limit of the aforesaid range may be more than adequate, while in other cases still larger doses may be employed. Therefore, the above dosage range is not intended to limit the scope of the invention in any way. This invention also provides a compound of Formula I, or a pharmaceutically acceptable salt thereof, for use as a medicament.

Additionally, this invention provides use of a compound of Formula I, or a pharmaceutically acceptable salt thereof, in the manufacture of a medicament for treating cancer. In particular, the cancer is selected from the group consisting of brain cancer, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer and melanoma.

Furthermore, this invention provides a pharmaceutical composition comprising a compound of Formula I, or a pharmaceutically acceptable salt thereof, as an active ingredient for treating brain cancer, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer or melanoma.

The compounds of Formula I, or salts thereof, may be prepared by a variety of procedures known in the art, as well as those described in the Schemes, Preparations, and Examples below. The specific synthetic steps for each of the routes described may be combined in different ways, or in conjunction with steps from different schemes, to prepare compounds of Formula I, or salts thereof.

The substituents, unless otherwise indicated, are as previously defined. The reagents and starting materials are generally readily available to one of ordinary skill in the art. Others may be made by standard techniques of organic and heterocyclic chemistry, techniques which are analogous to the syntheses of known structurally-similar compounds, and the procedures described in the Preparations and Examples which follow including any novel procedures.

As used herein, the following terms have the meanings indicated: "boc" or "t-boc" refers to tert-butoxycarbonyl; "BOP" refers to benzotriazole-1-yl-oxy-tris-(dimethylamino)-phosphonium hexafluorophosphate; "DMA" refers to N,N-dimethylacetamide; "DMF" refers to N,N-dimethylformamide; "DMSO" refers to methylsulfoxide; "EDCI" refers to 1-(3-dimethylaminopropyl)-3-ethylcarbodiimide hydrochloride; "Et$_2$O" refers to diethyl ether; "EtOAc" refers to ethyl acetate; "iPrOH" refers to isopropanol; "MeOH" refers to methanol; "TFA" refers to trifluoroacetic acid; "SCX" refers to strong cation exchange; "PyBOP" refers to benzotriazol-1-yloxytripyrrolidino-phosphonium hexafluorophosphate; and "IC$_{50}$" refers to the concentration of an agent that produces 50% of the maximal inhibitory response possible for that agent.

Scheme 1

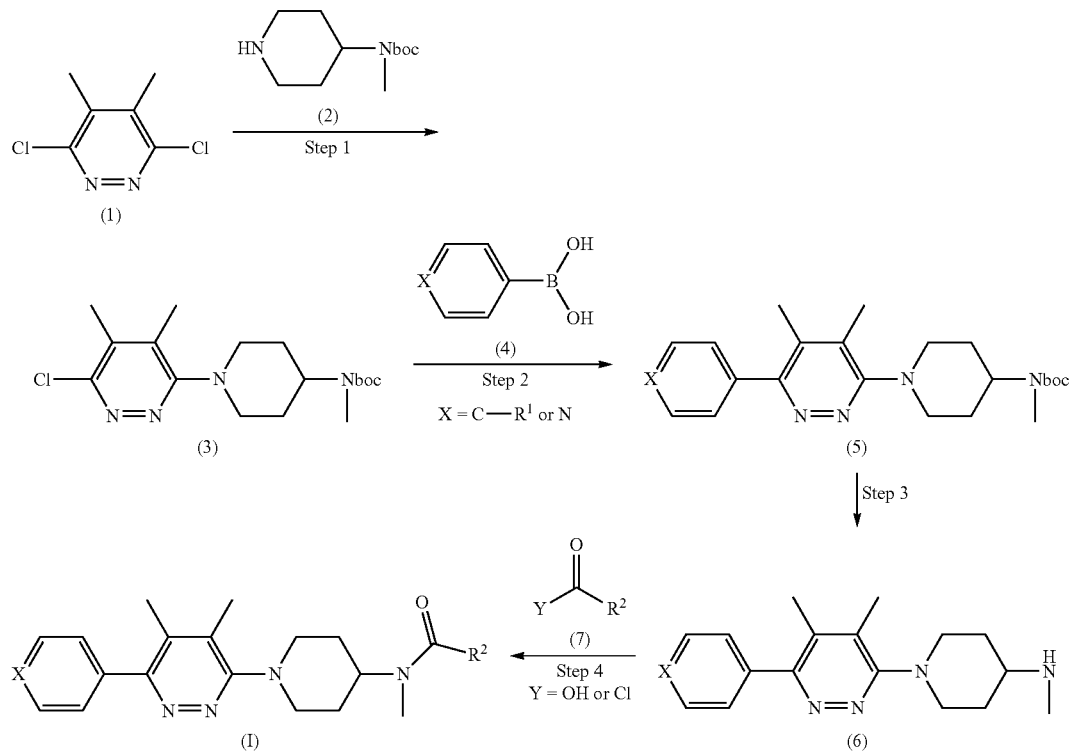

A compound of Formula I can be prepared in accordance with reactions as depicted in Scheme 1.

In Scheme 1, Step 1,3,6-dichloro-4,5-dimethylpyridazine (1) is displaced with tert-butyl methyl(piperidin-4-yl)carbamate (2) in a nucleophilic aromatic substitution reaction (SNAr) in a polar aprotic solvent such as DMF, DMA, or DMSO in the presence of an organic base such as triethylamine and/or diisopropylethylamine and/or an inorganic base such as potassium carbonate with heating to 100-140° C. to provide tert-butyl 1-(6-chloro-4,5-dimethylpyridazin-3-yl)piperidin-4-yl(methyl)carbamate (3). In Step 2, the remaining chloride on the dimethylpyridazine can be reacted with an aryl boronic acid (4) in a Suzuki-Miyaura cross coupling reaction to give the corresponding 4,5-dimethyl-6-substituted arylpyridazine-3-substituted piperidine (5). The skilled artisan will recognize that there are a variety of conditions useful for facilitating such cross-coupling reactions. The reaction conditions make use of a suitable solvent such as dioxane or dioxane/water in the presence of a base such as cesium carbonate or cesium fluoride and a palladium catalyst such as (1,1'-bis(diphenylphosphino)ferrocene)palladium(II) chloride or (SP-4-1)-bis[bis(1,1-dimethylethyl)(4-methoxyphenyl)phosphine-κP]dichloro-palladium (prepared according to *J. Org. Chem.* 2007, 72, 5104-5112) under an inert atmosphere at a temperature of about 80-160° C. to give a compound of formula (5). The amine can be deprotected by standard deprotection methods. Methods for introducing and removing nitrogen protecting groups are well known in the art (see, e.g., Greene and Wuts, *Protective Groups in Organic Synthesis*, 3$^{rd}$ Ed., John Wiley and Sons, New York, (1999)). For example, boc deprotection of the amine of formula (5) can be accomplished under acidic conditions, such as hydrogen chloride or trifluoroacetic acid to give a compound of formula (6). Acylation of the amine in Step 4 can be accomplished with a substituted acid chloride (7) in an inert solvent such as dichloromethane or alternatively, a compound of formula (6) can be acylated using a substituted carboxylic acid and an appropriate coupling reagent such as PyBOP, pentafluorophenyl diphenylphosphinate, BOP, or EDCI and an appropriate base such as triethylamine or diisopropylethylamine in a suitable solvent such as DMF and/or DMSO, or dichloromethane to give neutral compounds of Formula I. Compounds of Formula I can be converted to a salt such as the HCl salt by methods known to one skilled in the art such as adding HCl in Et$_2$O or the HCl can be generated in situ by dropwise addition of acetyl chloride to a solution of an alcohol solvent such as methanol at 0-20° C.

Scheme 2

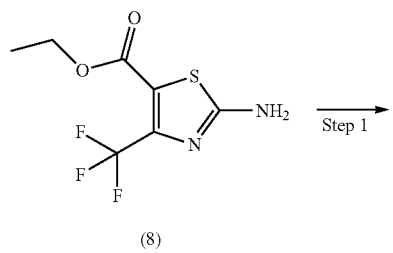

(8)

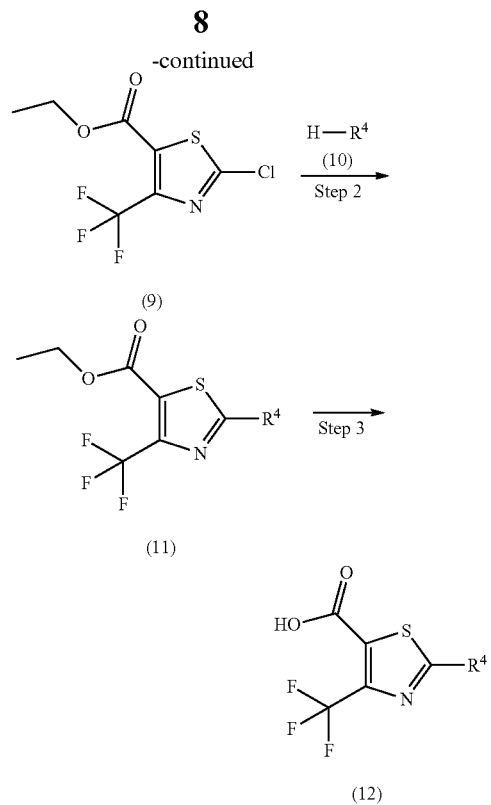

(9)

(11)

(12)

The desired carboxylic acids (7), (Y=OH, Step 4, Scheme 1), can be prepared as shown in Scheme 2. The primary amine at the 2-position of the thiazole (8) is displaced with a chloride in a Sandmeyer reaction using copper chloride and isopentyl nitrite in an appropriate solvent such as acetonitrile as shown in Step 1 to give a 2-chloro-4,5-substituted thiazole (9). The chloride is then displaced with the desired amine (10) in Step 2 in a polar aprotic solvent such as DMSO to give the corresponding amino thiazole (11). Hydrolysis of the ester in Step 3 with a suitable base such as aqueous sodium hydroxide or aqueous lithium hydroxide in a suitable solvent such as MeOH or dioxane gives the desired carboxylic acid (12).

Scheme 3

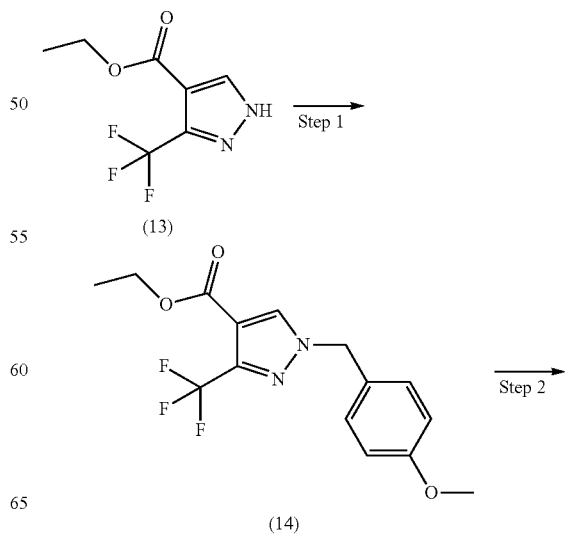

(13)

(14)

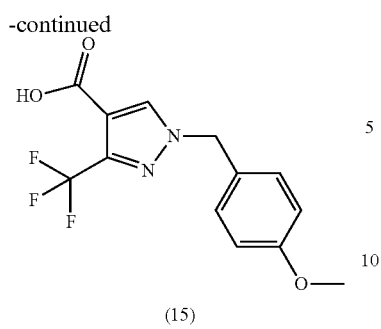

(15)

In a further example of preparing the desired carboxylic acid (7), (Y=OH, Step 4, Scheme 1), as shown in Scheme 3, a pyrazole (13) is protected with a suitable protecting group such 4-methoxybenzyl as shown in Step 1 using an inorganic base such as potassium carbonate in a solvent such as acetone to give the protected pyrazole (14). The ester is then hydrolyzed with a suitable base as shown in Step 3 to give a compound of formula (15). Following acylation at Step 4, Scheme 1, deprotection of the pyrazole can be completed under acidic conditions such as TFA to give compounds of Formula 1.

Scheme 4 shows a still further example of preparing a carboxylic acid (7), (Y=OH, Step 4, Scheme 1).

Scheme 4

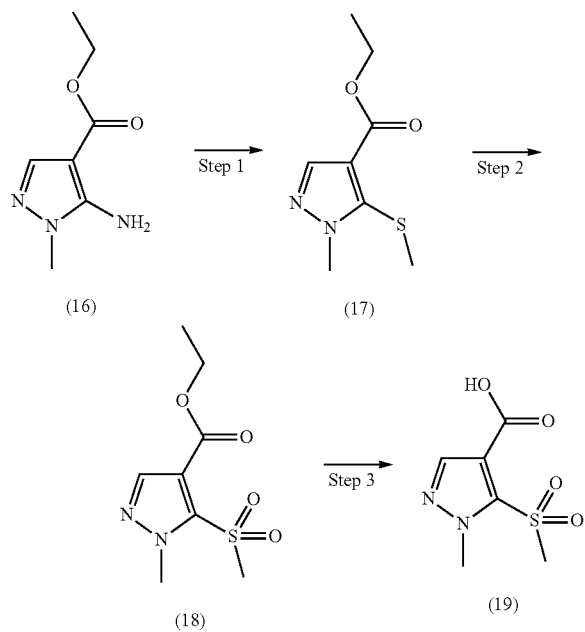

Isopentyl nitrite can be added dropwise to a solution of an amino pyrazole (16) and dimethyl disulfide in an inert solvent such as chloroform to convert the primary amine to a thiomethyl group to form ethyl 1-methyl-5-(methylthio)-1H-pyrazole-4-carboxylate (17) as shown in Step 1. The thiomethyl group of compound (17) can be oxidized to the methylsulfone with an oxidizing agent such as hydrogen peroxide in an appropriate solvent such as acetic acid to give a compound of formula 18, Step 2. Hydrolysis of the ester as previously described gives the appropriate carboxylic acid as shown in Step 3, compound (7).

The following Preparations and Examples are provided to illustrate the invention in further detail and represent typical syntheses of the compounds of Formula (I). The names of the compounds of the present invention are generally provided by ChemDraw Ultra® 10.0.

Preparation 1 tert-Butyl 1-(6-chloro-4,5-dimethylpyridazin-3-yl)piperidin-4-yl(methyl)carbamate

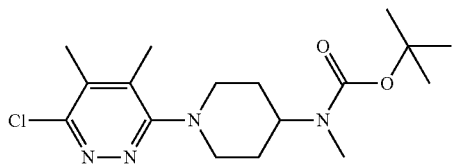 [SMILES: Cc1c(Cl)nnc(N2CCC(N(C)C(=O)OC(C)(C)C)CC2)c1C]

Heat a mixture of 3,6-dichloro-4,5-dimethylpyridazine (11.0 g, 62.1 mmol), tert-butyl methyl(piperidin-4-yl)carbamate (23.3 g, 109 mmol), and powdered $K_2CO_3$ (17.2 g, 124 mmol) in DMSO (310 mL) at 120° C. for 2 d. Cool the reaction mixture, dilute with $H_2O$, and filter off the solid. Rinse the solid with $H_2O$, and dry under vacuum at 45° C. Dissolve the solid in $CH_2Cl_2$, and pass the solution through a pad of silica gel, eluting with $CH_2Cl_2$. Concentrate the organic layer under reduced pressure to obtain the title compound as a yellow solid (14.3 g, 65%). ES/MS m/z ($^{35}Cl$) 355.0 (M+1).

Preparation 2 tert-Butyl 1-(6-(4-fluorophenyl)-4,5-dimethylpyridazin-3-yl)piperidin-4-yl(methyl)carbamate

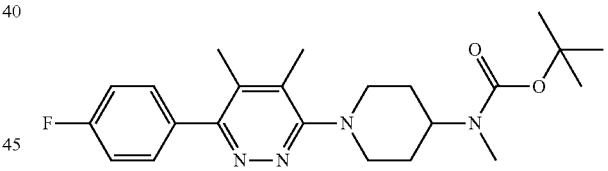

Heat a mixture of tert-butyl 1-(6-chloro-4,5-dimethylpyridazin-3-yl)piperidin-4-yl(methyl)carbamate (1.5 g, 4.23 mmol), 4-fluorophenylboronic acid (887 mg, 6.34 mmol), $Cs_2CO_3$ (5.51 g, 16.9 mmol) and (SP-4-1)-bis[bis(1,1-dimethylethyl)(4-methoxyphenyl)phosphine-κP]dichloro-palladium (J. Org. Chem. 2007, 72, 5104-5112) (29 mg, 0.042 mmol) in a mixture of 1,4-dioxane (30 mL) and $H_2O$ (10 mL) under $N_2$ at 90° C. overnight. Partition the reaction mixture between $H_2O$ and $CH_2Cl_2$. Separate the layers, and extract the aqueous layer with $CH_2Cl_2$. Combine the organic layers, dry over $Na_2SO_4$, filter, and concentrate under reduced pressure. Purify the residue by flash silica gel chromatography (gradient of 0 to 2% 2 M $NH_3$/MeOH in $CH_2Cl_2$) to provide the title compound as a white foam (1.05 g, 60%). ES/MS m/z 415.2 (M+1).

Alternate Procedure:

Treat a $N_2$ degassed mixture of tert-butyl 1-(6-chloro-4,5-dimethylpyridazin-3-yl)piperidin-4-yl(methyl)carbamate (3.01 g, 8.48 mmol), 4-fluorophenylboronic acid (1.23 g, 8.80 mmol) and CsF (4.08 g, 26.8 mmol) in 1,4-dioxane (80 mL)

Preparation 3 tert-Butyl 1-(6-(4-cyanophenyl)-4,5-dimethylpyridazin-3-yl)piperidin-4-yl(methyl)carbamate

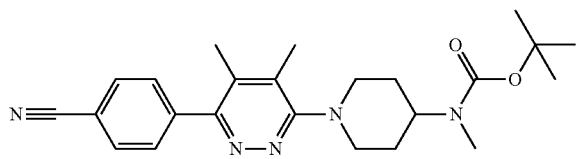 [SMILES: Cc1c(-c2ccc(C#N)cc2)nnc(N2CCC(N(C)C(=O)OC(C)(C)C)CC2)c1C]

Heat a mixture of tert-butyl 1-(6-chloro-4,5-dimethylpyridazin-3-yl)piperidin-4-yl(methyl)carbamate (1.5 g, 4.23 mmol), 4-cyanophenylboronic acid (932 mg, 6.34 mmol), Cs$_2$CO$_3$ (5.51 g, 16.9 mmol) and (SP-4-1)-bis[bis(1,1-dimethylethyl)(4-methoxyphenyl)phosphine-κP]dichloro-palladium (29 mg, 0.042 mmol) in a mixture of 1,4-dioxane (30 mL) and H$_2$O (10 mL) under N$_2$ at 90° C. overnight. Partition the reaction mixture between EtOAc and H$_2$O with dissolved NaHCO$_3$. Separate the layers, and extract the aqueous layer with EtOAc. Combine the organic layers, dry over Na$_2$SO$_4$, filter, and concentrate under reduced pressure. Purify the residue by flash silica gel chromatography (gradient of 0 to 2% 2 M NH$_3$/MeOH in CH$_2$Cl$_2$) to provide the title compound as a yellow solid (1.68 g, 94%). ES/MS m/z 422.2 (M+1).

Prepare the substituted phenylpyridazines in the table below by essentially following the procedure described in Preparation 3, using the appropriately substituted aryl boronic acid. For Preparation 5, directly filter the crude reaction mixture over a pad of silica gel eluting with 5% M NH$_3$/MeOH in CH$_2$Cl$_2$. Concentrate the eluent and purify without an aqueous work-up.

Preparation 6

1-(6-(4-Fluorophenyl)-4,5-dimethylpyridazin-3-yl)-N-methylpiperidin-4-amine

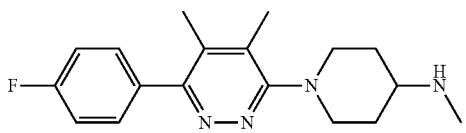

Treat a solution of tert-butyl 1-(6-(4-fluorophenyl)-4,5-dimethylpyridazin-3-yl)piperidin-4-yl(methyl)carbamate (1.04 g, 2.51 mmol) in 1,4-dioxane (10 mL) with 4 M HCl in 1,4-dioxane (15.0 mL). Stir the resulting mixture at ambient temperature for 2 h. Concentrate the reaction mixture under reduced pressure. Dissolve the residue in MeOH, and pour onto an SCX column (Varian, 10 g). Rinse the column with MeOH and CH$_2$Cl$_2$, and elute the product with a 1:1 mixture of CH$_2$Cl$_2$ and 2 M NH$_3$/MeOH. Concentrate under reduced pressure to afford the title compound as an off-white solid (784 mg, 99%). ES/MS m/z 315.2 (M+1).

Preparation 7

4-(4,5-Dimethyl-6-(4-(methylamino)piperidin-1-yl)pyridazin-3-yl)benzonitrile

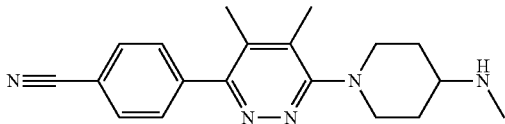

Treat a solution of tert-butyl 1-(6-(4-cyanophenyl)-4,5-dimethylpyridazin-3-yl)piperidin-4-yl(methyl)carbamate (1.68 g, 3.99 mmol) in 1,4-dioxane (20 mL) with 4 M HCl in 1,4-dioxane (20 mL). Stir the resulting mixture at ambient temperature for 2 h. Concentrate the reaction mixture under reduced pressure. Dissolve the residue in MeOH, and pour onto an SCX column (Varian, 20 g). Rinse the column with MeOH and CH$_2$Cl$_2$, and elute the product with a 1:1 mixture

| Prep. No. | Chemical Name | Structure | ES/MS m/z |
|---|---|---|---|
| 4 | tert-Butyl 1-(4,5-dimethyl-6-phenylpyridazin-3-yl)piperidin-4-yl(methyl)carbamate | 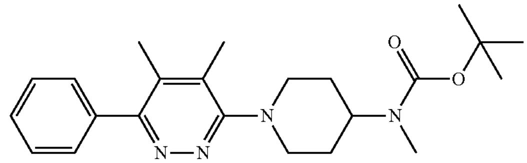 [SMILES: Cc1c(-c2ccccc2)nnc(N2CCC(N(C)C(=O)OC(C)(C)C)CC2)c1C] | 397.2 (M + 1) |
| 5 | tert-Butyl-1-(4,5-dimethyl-6-(pyridine-4-yl)pyridazin-3-yl)piperidin-4-yl(methyl)carbamate | | 398.2 (M + 1) | of CH$_2$Cl$_2$ and 2 M NH$_3$/MeOH. Concentrate under reduced pressure to afford the title compound as a yellow solid (1.28 g, quantitative). ES/MS m/z 322.2 (M+1).

Prepare the deprotected N-methylaminopiperidine in the table below by essentially following the procedure described in Preparation 7, using the appropriate boc-protected piperidine.

| Prep. No. | Chemical Name | Structure | ES/MS m/z |
|---|---|---|---|
| 8 | 1-(4,5-Dimethyl-6-phenylpyridazin-3-yl)-N-methylpiperidin-4-amine | 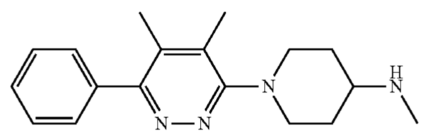 [SMILES: CNC1CCN(c2nnc(-c3ccccc3)c(C)c2C)CC1] | 297.2 (M + 1) |

Slowly treat a 0° C. mixture of CuCl$_2$ (671 mg, 4.99 mmol) and isopentyl nitrite (732 mg, 6.24 mmol) in acetonitrile (10 mL) with ethyl 2-amino-4-(trifluoromethyl)thiazole-5-carboxylate (1.0 g, 4.16 mmol). Stir the resulting mixture at ambient temperature for 1 h. Heat to 50° C. for 1 h. Remove most of the solvents, and pour into a mixture of ice and concentrated HCl. Extract with CH$_2$Cl$_2$. Wash the organic layer with brine, dry over Na$_2$SO$_4$, filter, and concentrate under reduced pressure. Purify the resulting residue by flash silica gel chromatography (20:1 hexanes:EtOAc) to give the title compound (762 mg, 71%). $^1$H NMR (300 MHz, DMSO-d$_6$) δ 1.26 (t, J=7.0 Hz, 3H), 4.31 (q, J=7.0 Hz, 2H).

Preparation 9

1-(4,5-Dimethyl-6-(pyridine-4-yl)pyridazin-3-yl)-N-methylpiperidin-4-amine

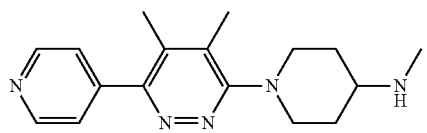 [SMILES: CNC1CCN(c2nnc(-c3ccncc3)c(C)c2C)CC1]

Add CH$_2$Cl$_2$ (20 mL) and trifluoroacetic acid (20 mL) to tert-butyl-1-(4,5-dimethyl-6-(pyridine-4-yl)pyridazin-3-yl)piperidin-4-yl(methyl)carbamate (1.19 g, 2.99 mmol). Stir at ambient temperature for 3 d. Concentrate under reduced pressure to give a residue. Partition the residue between CH$_2$Cl$_2$ and 1 N NaOH. Separate the layers, and extract the aqueous layer twice with CH$_2$Cl$_2$. Combine the organic extracts, dry over Na$_2$SO$_4$, filter, and concentrate under reduced pressure to obtain the title compound (790 mg, 89%). ES/MS m/z 298.2 (M+1).

Preparation 10

Ethyl 2-chloro-4-(trifluoromethyl)thiazole-5-carboxylate

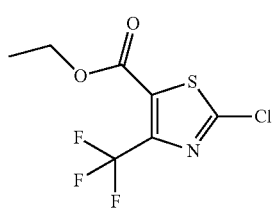

Preparation 11

Ethyl 2-morpholino-4-(trifluoromethyl)thiazole-5-carboxylate

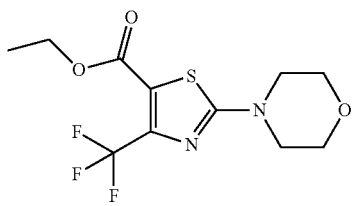 [SMILES: CCOC(=O)c1sc(N2CCOCC2)nc1C(F)(F)F]

Add ethyl 2-chloro-4-(trifluoromethyl)thiazole-5-carboxylate (4.00 g, 15.4 mmol) to a solution of morpholine (4.03 g, 46.2 mmol) in DMSO (10 mL). Stir the reaction at ambient temperature overnight. Add CH$_2$Cl$_2$, and wash the mixture with H$_2$O. Dry the organic phase over Na$_2$SO$_4$, filter, and concentrate under reduced pressure. Purify the resulting residue by flash silica gel chromatography (20:5:1 hexanes:EtOAc:2 M NH$_3$/MeOH) to yield the title compound (4.58 g, 96%). ES/MS m/z 311.0 (M+1).

Prepare the amino thiazole esters in the table below by essentially following the procedure as described in Preparation 11, using the appropriate amine.

| Prep. No. | Chemical Name | Structure | ES/MS m/z |
|---|---|---|---|
| 12 | Ethyl 2-(dimethylamino)-4-(trifluoromethyl)thiazole-5-carboxylate | 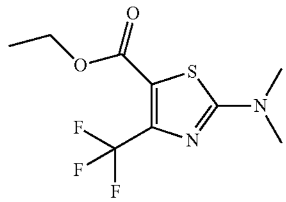 [SMILES: CCOC(=O)c1sc(N(C)C)nc1C(F)(F)F] | 269.0 (M + 1) |
| 13 | Ethyl 2-(diethylamino)-4-(trifluoromethyl)thiazole-5-carboxylate | 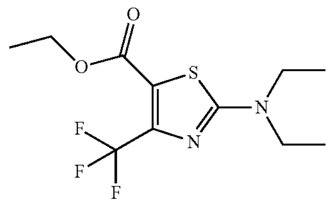 [SMILES: CCOC(=O)c1sc(N(CC)CC)nc1C(F)(F)F] | 297.0 (M + 1) |
| 14 | Ethyl 2-(pyrrolidin-1-yl)-4-(trifluoromethyl)thiazole-5-carboxylate | 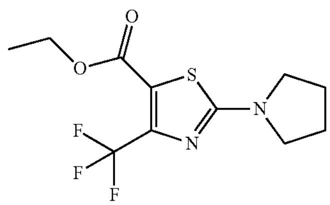 [SMILES: CCOC(=O)c1sc(N2CCCC2)nc1C(F)(F)F] | 295.0 (M + 1) |

Preparation 15

2-Morpholino-4-(trifluoromethyl)thiazole-5-carboxylic acid

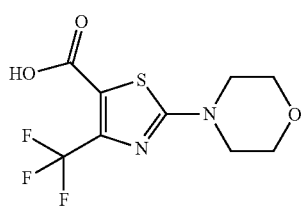 [SMILES: O=C(O)c1sc(N2CCOCC2)nc1C(F)(F)F]

Add ethyl 2-morpholino-4-(trifluoromethyl)thiazole-5-carboxylate (4.58 g, 14.8 mmol) to a mixture of 1 N NaOH (20 mL) in MeOH (20 mL), and heat the reaction to 50° C. for 1 h. Concentrate the reaction under reduced pressure, and add $H_2O$ to the residue. Acidify the mixture to pH 4, and filter the solid. Wash the solid with $H_2O$, and dry to obtain the title compound (4.13 g, 99%). ES/MS m/z 283.0 (M+1).

Prepare the amino thiazole acids in the table below by essentially following the procedure as described in Preparation 15, using the appropriate ester.

| Prep. No. | Chemical Name | Structure | ES/MS m/z |
|---|---|---|---|
| 16 | 2-(Dimethylamino)-4-(trifluoromethyl)thiazole-5-carboxylic acid | 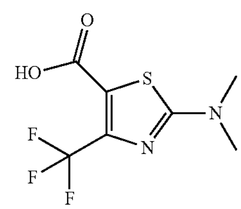 | 240.0 (M + 1) |
| 17 | 2-(Diethylamino)-4-(trifluoromethyl)thiazole-5-carboxylic acid | 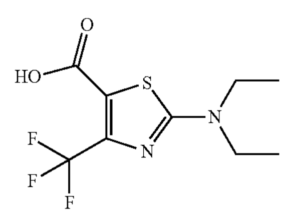 [SMILES: CCN(CC)c1nc(C(F)(F)F)c(C(=O)O)s1] | 269.0 (M + 1) |
| 18 | 2-(Pyrrolidin-1-yl)-4-(trifluoromethyl)thiazole-5-carboxylic acid | 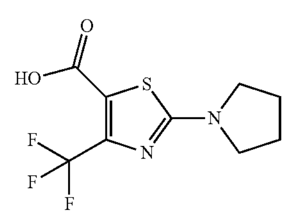 [SMILES: O=C(O)c1sc(N2CCCC2)nc1C(F)(F)F] | 267.0 (M + 1) |

Preparation 19

(S)-tert-Butyl 2-((1-(6-(4-fluorophenyl)-4,5-dimethylpyridazin-3-yl)piperidin-4-yl)(methyl)carbamoyl)piperidine-1-carboxylate

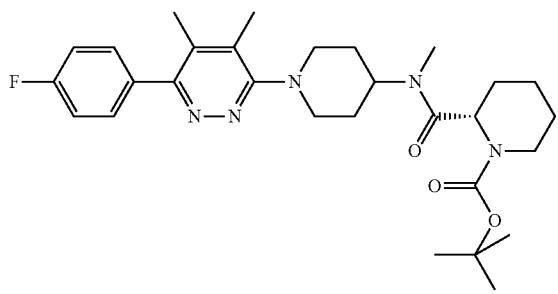 [SMILES: Cc1c(-c2ccc(F)cc2)nnc(N2CCC(N(C)C(=O)[C@@H]3CCCCN3C(=O)OC(C)(C)C)CC2)c1C]

Sequentially treat a solution of 1-(6-(4-fluorophenyl)-4,5-dimethylpyridazin-3-yl)-N-methylpiperidin-4-amine (100 mg, 0.318 mmol) in $CH_2Cl_2$ (3.2 mL) with (S)-1-(tert-butoxycarbonyl)piperidine-2-carboxylic acid (109 mg, 0.477 mmol), triethylamine (0.067 mL, 0.477 mmol) and EDCI (92 mg, 0.477 mmol). Stir the resulting mixture at ambient temperature for 2 d. Pour the reaction mixture into $H_2O$ containing $NaHCO_3$. Separate the layers, and extract the aqueous layer with $CH_2Cl_2$. Combine the organic layers, dry over $Na_2SO_4$, filter, and concentrate under reduced pressure. Purify the residue by flash silica gel chromatography (gradient of 0 to 2% 2 M $NH_3$/MeOH in $CH_2Cl_2$) to afford the title compound as a white solid (82 mg, 49%). ES/MS m/z 526.2 (M+1).

Preparation 20

Ethyl 1-(4-methoxybenzyl)-3-(trifluoromethyl)-1H-pyrazole-4-carboxylate

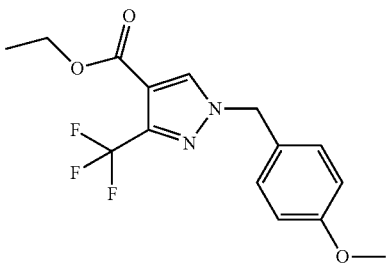 [SMILES: CCOC(=O)c1cn(Cc2ccc(OC)cc2)nc1C(F)(F)F]

Add $K_2CO_3$ (503 mg, 3.60 mmol) to a solution of ethyl 3-(trifluoromethyl)-1H-pyrazole-4-carboxylate (500 mg, 2.40 mmol) in acetone (8 mL) at ambient temperature under $N_2$. Add 1-bromomethyl-4-methoxybenzene (0.51 mL, 3.6 mmol) dropwise to the mixture, and stir overnight under $N_2$. Quench the reaction with $H_2O$, and extract twice with EtOAc. Dry the combined organic layers over $MgSO_4$, filter, and concentrate under reduced pressure. Purify the residue by flash silica gel chromatography (gradient of 0 to 15% EtOAc in hexanes) to yield the title compound (789 mg, quantitative). ES/MS m/z 351.0 (M+Na).

Preparation 21

1-(4-Methoxybenzyl)-3-(trifluoromethyl)-1H-pyrazole-4-carboxylic acid

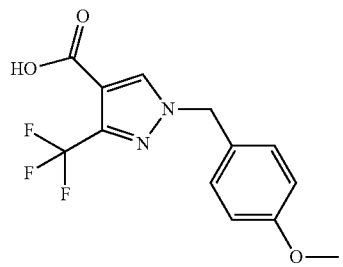 [SMILES: COc1ccc(Cn2cc(C(=O)O)c(C(F)(F)F)n2)cc1]

Add a solution of LiOH (122 mg, 5.03 mmol) in $H_2O$ (3 mL) to a stirred solution of ethyl 1-(4-methoxybenzyl)-3-(trifluoromethyl)-1H-pyrazole-4-carboxylate (550 mg, 1.68 mmol) in 1,4-dioxane (10 mL). Stir overnight at ambient temperature. Acidify to pH 5 with 1 N HCl and extract with $CH_2Cl_2$ and 2× with 20% iPrOH in $CHCl_3$. Dry the combined organic layers with $MgSO_4$, filter and concentrate under reduced pressure to obtain 140 mg of the title compound as a white solid. Acidify the aqueous layer to pH 2-3 with 1 N HCl, and extract twice with 20% iPrOH in $CHCl_3$. Dry the combined organics over $MgSO_4$, filter, and add the solution to the initially obtained 140 mg white solids. Concentrate to afford the title compound as a white solid (426 mg, 85%). ES/MS m/z 299.0 (M−1).

Preparation 22

N-(1-(6-(4-Fluorophenyl)-4,5-dimethylpyridazin-3-yl)piperidin-4-yl)-1-(4-methoxybenzyl)-N-methyl-3-(trifluoromethyl)-1H-pyrazole-4-carboxamide

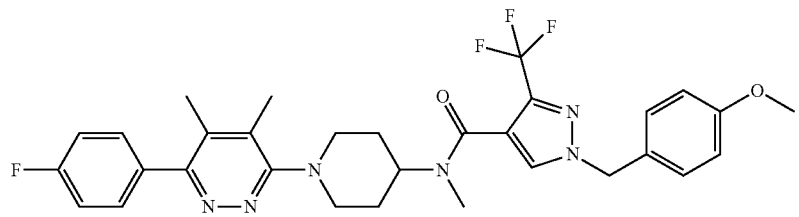 [SMILES: COc1ccc(Cn2cc(C(=O)N(C)C3CCN(c4nnc(-c5ccc(F)cc5)c(C)c4C)CC3)c(C(F)(F)F)n2)cc1]

Add PyBOP (343 mg, 0.65 mmol) and triethylamine (0.21 mL, 1.50 mmol) to a stirred solution of 1-(6-(4-fluorophenyl)-4,5-dimethylpyridazin-3-yl)-N-methylpiperidin-4-amine (157 mg, 0.50 mmol) and 1-(4-methoxybenzyl)-3-(trifluoromethyl)-1H-pyrazole-4-carboxylic acid (165 mg, 0.55 mmol) in anhydrous DMF (2.5 mL). Stir the resulting mixture at ambient temperature under $N_2$ overnight. Concentrate, add MeOH, filter solids, and concentrate the filtrate. Dilute the residue with MeOH, and pour onto an SCX column (Thermo Scientific, 10 g). Wash with MeOH, and then elute the product with 2 M $NH_3$/MeOH. Concentrate and purify by flash silica gel chromatography using a gradient of 0 to 10% (10% 2 M $NH_3$/MeOH in EtOAc) in hexanes to obtain the title compound as a white solid (170 mg, 43%). ES/MS m/z 597.0 (M+1).

Preparation 23

Ethyl 1-methyl-5-(methylthio)-1H-pyrazole-4-carboxylate

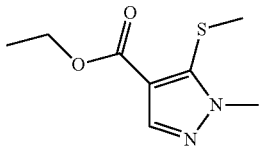

Add isopentyl nitrite (0.5 mL, 3.75 mmol) to a stirred 5° C. solution of ethyl 1-methyl-5-amino-1H-pyrazole-4-carboxylate (1.69 g, 10.0 mmol) and dimethyl disulfide (1.79 mL, 20.0 mmol) in $CHCl_3$ under nitrogen in a 3-necked flask equipped with a thermometer and a condenser. Allow the reaction to warm to 20° C. in a $H_2O$ bath, and treat with additional isopentyl nitrite (1.5 mL, 11.3 mmol) dropwise. After 15 min, remove the reaction from the 20° C. $H_2O$ bath (exotherm raises temperature to 50° C. over approximately 1 min). Stir at ambient temperature under $N_2$ overnight. Wash with $H_2O$, and separate the layers. Extract the aqueous layer with $CHCl_3$, combine the organic layers, dry over $MgSO_4$, filter, and concentrate under reduced pressure. Purify the residue by flash silica gel chromatography (gradient of 0 to 35% EtOAc in hexanes) to afford the title compound (1.94 g, 97%). ES/MS m/z 201.0 (M+1).

Preparation 24

Ethyl 1-methyl-5-(methylsulfonyl)-1H-pyrazole-4-carboxylate

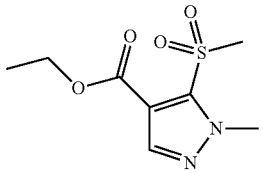

Combine ethyl 1-methyl-5-(methylthio)-1H-pyrazole-4-carboxylate (1.68 g, 8.39 mmol), glacial acetic acid (11 mL), and hydrogen peroxide (5.10 mL, 50.3 mmol) and heat the resulting mixture at 100° C. for 1.5 h. Allow the reaction to cool to ambient temperature and stir overnight. Add ice and extract twice with $CH_2Cl_2$. Combine the organic layers, dry over $MgSO_4$, filter, and concentrate under reduced pressure. Purify the residue by flash silica gel chromatography (gradient of 0 to 50% EtOAc in hexanes) to provide the title compound (1.95 g, 100%). ES/MS m/z 233.0 (M+1).

Preparation 25

1-Methyl-5-(methylsulfonyl)-1H-pyrazole-4-carboxylic acid

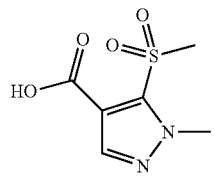

Add a solution of LiOH (22 mg, 0.90 mmol) in $H_2O$ (1 mL) to a rapidly stirring solution of ethyl 1-methyl-5-(methylsulfonyl)-1H-pyrazole-4-carboxylate (175 mg, 0.75 mmol) in 1,4-dioxane (3 mL) at ambient temperature. Treat the reaction mixture with additional LiOH (5 mg, 0.21 mmol), and stir overnight. Acidify to pH 2 with 1 N HCl, and extract twice with $CH_2Cl_2$. Combine the organic layers, dry over $MgSO_4$, filter, and concentrate under reduced pressure to yield the title compound as a white solid (98 mg, 64%). ES/MS m/z 202.9 (M−1).

EXAMPLE 1

4-Cyano-N-(1-(6-(4-cyanophenyl)-4,5-dimethylpyridazin-3-yl)piperidin-4-yl)-N-methylbenzamide hydrochloride

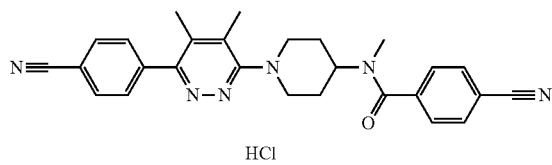 [SMILES: Cc1c(-c2ccc(C#N)cc2)nnc(N2CCC(N(C)C(=O)c3ccc(C#N)cc3)CC2)c1C ; Cl]

Treat a solution of 4-(4,5-dimethyl-6-(4-(methylamino)piperidin-1-yl)pyridazin-3-yl)benzonitrile (90 mg, 0.28 mmol) and triethylamine (0.12 mL, 0.84 mmol) in $CH_2Cl_2$ (2.8 mL) with 4-cyanobenzoyl chloride (56 mg, 0.34 mmol). Stir the reaction at ambient temperature overnight. Wash with $H_2O$ and separate the layers. Directly purify the organic layer by flash silica gel chromatography (gradient of 0 to 2% 2 M $NH_3$/MeOH in $CH_2Cl_2$). Concentrate to afford a white solid. Dissolve the material in MeOH and add 1.1 eq of methanolic HCl (preform by dripping acetyl chloride into MeOH). Concentrate the mixture under a stream of $N_2$ gas and dry the residue in a vacuum oven at 45° C. to obtain the title compound as yellow solid (130 mg, 95%). ES/MS m/z 451.2 (M+1).

Prepare the piperadinylamides in the table below by essentially following the procedure described in Example 1, using the appropriate acid chloride with reaction times ranging from 6 h to 3 d. For Examples 7, 8 and 13, use excess 1 M HCl in $Et_2O$ to form the salts. For Example 10, use 3 equivalents of preformed methanolic HCl to form the salt.

| Ex. No. | Chemical Name | Structure | ES/MS m/z |
|---|---|---|---|
| 2 | N-(1-(4,5-Dimethyl-6-phenylpyridazin-3-yl)piperidin-4-yl)-4-fluoro-N-methyl-2-(trifluoromethyl)benzamide hydrochloride | 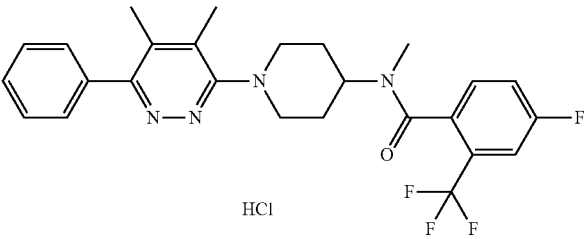 [SMILES: Cc1c(-c2ccccc2)nnc(N2CCC(N(C)C(=O)c3ccc(F)cc3C(F)(F)F)CC2)c1C ; Cl] | 487.2 (M + 1) |
| 3 | N-(1-(6-(4-Fluorophenyl)-4,5-dimethylpyridazin-3-yl)piperidin-4-yl)-N-methyl-2-(trifluoromethyl)benzamide hydrochloride | 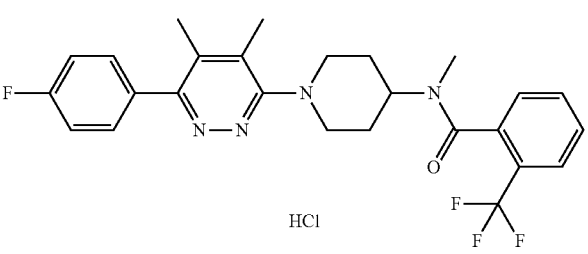 [SMILES: Cc1c(-c2ccc(F)cc2)nnc(N2CCC(N(C)C(=O)c3ccccc3C(F)(F)F)CC2)c1C ; Cl] | 487.2 (M + 1) |
| 4 | N-(1-(6-(4-Cyanophenyl)-4,5-dimethylpyridazin-3-yl)piperidin-4-yl)-N-methyl-4-(trifluoromethoxy)benzamide hydrochloride | 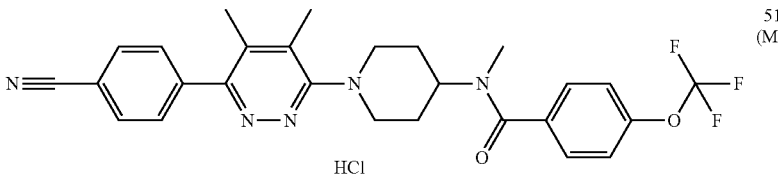 | 510.2 (M + 1) |
| 5 | 4-Cyano-N-(1-(6-(4-fluorophenyl)-4,5-dimethylpyridazin-3-yl)piperidin-4-yl)-N-methylbenzamide hydrochloride | 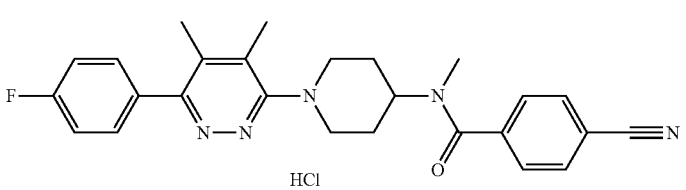 | 444.2 (M + 1) |
| 6 | N-(1-(4,5-Dimethyl-6-phenylpyridazin-3-yl)piperidin-4-yl)-N-methyl-2-(trifluoromethyl)benzamide hydrochloride | 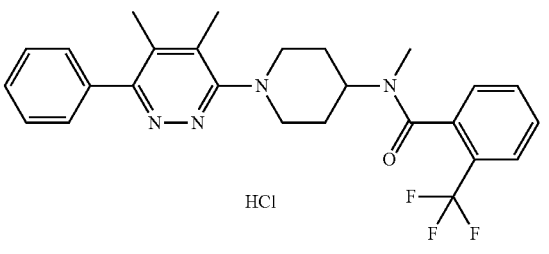 [SMILES: Cc1c(-c2ccccc2)nnc(N2CCC(N(C)C(=O)c3ccccc3C(F)(F)F)CC2)c1C ; Cl] | 469.2 (M + 1) |
| 7 | N-(1-(6-(4-Fluorophenyl)-4,5-dimethylpyridazin-3-yl)piperidin-4-yl)-N-methyl-4-(trifluoromethoxy)benzamide hydrochloride | 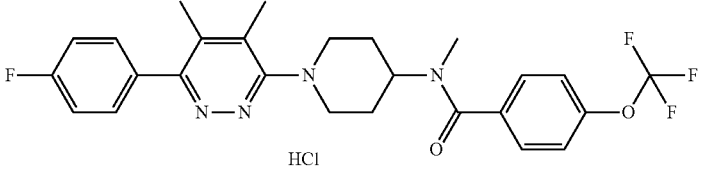 [SMILES: Cc1c(-c2ccc(F)cc2)nnc(N2CCC(N(C)C(=O)c3ccc(OC(F)(F)F)cc3)CC2)c1C ; Cl] | 503.2 (M + 1) |
| 8 | 2,4-Difluoro-N-(1-(6-(4-fluorophenyl)-4,5-dimethylpyridazin-3-yl)piperidin-4-yl)-N-methylbenzamide hydrochloride | 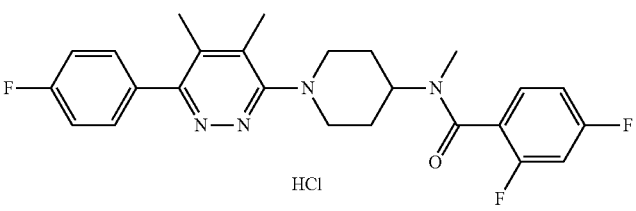 [SMILES: Cc1c(-c2ccc(F)cc2)nnc(N2CCC(N(C)C(=O)c3ccc(F)cc3F)CC2)c1C ; Cl] | 455.0 (M + 1) |

| Ex. No. | Chemical Name | Structure | ES/MS m/z |
|---|---|---|---|
| 9 | 3-Cyano-N-(1-(6-(4-cyanophenyl)-4,5-dimethylpyridazin-3-yl)piperidin-4-yl)-N-methylbenzamide hydrochloride | 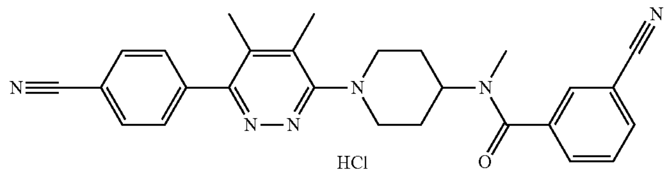 [SMILES: Cc1c(-c2ccc(C#N)cc2)nnc(N2CCC(N(C)C(=O)c3cccc(C#N)c3)CC2)c1C ; Cl] | 451.2 (M + 1) |
| 10 | N-(1-(6-(4-Cyanophenyl)-4,5-dimethylpyridazin-3-yl)piperidin-4-yl)-N-methyl-6-(trifluoromethyl)nicotinamide hydrochloride | 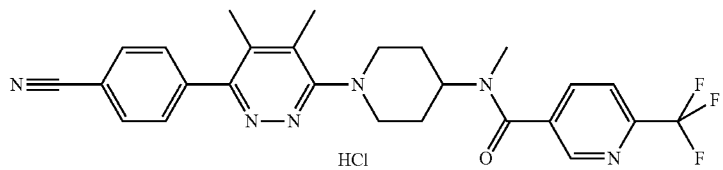 [SMILES: Cc1c(-c2ccc(C#N)cc2)nnc(N2CCC(N(C)C(=O)c3ccc(C(F)(F)F)nc3)CC2)c1C ; Cl] | 495.2 (M + 1) |
| 11 | 3-Cyano-N-(1-(6-(4-fluorophenyl)-4,5-dimethylpyridazin-3-yl)piperidin-4-yl)-N-methylbenzamide hydrochloride | 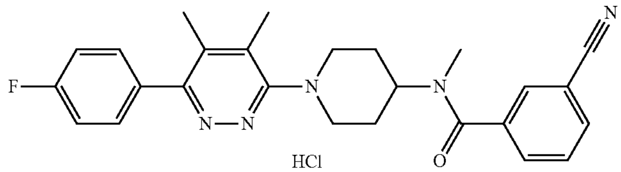 [SMILES: Cc1c(-c2ccc(F)cc2)nnc(N2CCC(N(C)C(=O)c3cccc(C#N)c3)CC2)c1C ; Cl] | 444.2 (M + 1) |
| 12 | 4-Cyano-N-(1-(4,5-dimethyl-6-phenylpyridazin-3-yl)piperidin-4-yl)-N-methylbenzamide hydrochloride | 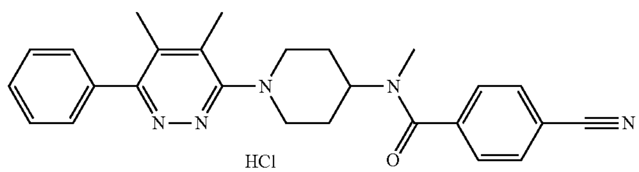 [SMILES: Cc1c(-c2ccccc2)nnc(N2CCC(N(C)C(=O)c3ccc(C#N)cc3)CC2)c1C ; Cl] | 426.2 (M + 1) |
| 13 | 2,4,6-Trifluoro-N-(1-(6-(4-fluorophenyl)-4,5-dimethylpyridazin-3-yl)piperidin-4-yl)-N-methylbenzamide hydrochloride | 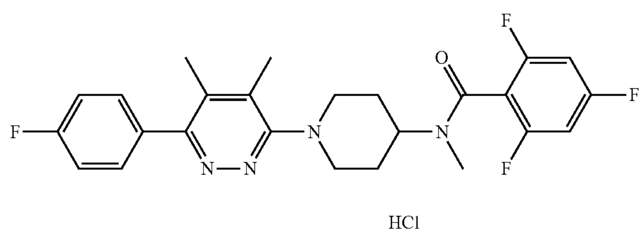 [SMILES: Cc1c(-c2ccc(F)cc2)nnc(N2CCC(N(C)C(=O)c3c(F)cc(F)cc3F)CC2)c1C ; Cl] | 473.0 (M + 1) |

EXAMPLE 14

N-(1-(6-(4-Cyanophenyl)-4,5-dimethylpyridazin-3-yl)piperidin-4-yl)-N-methyl-2-(trifluoromethyl)nicotinamide dihydrochloride

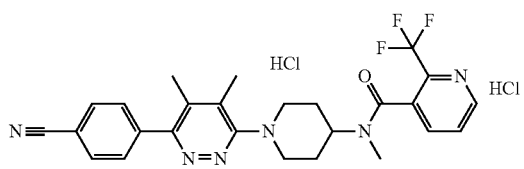 [SMILES: Cc1c(-c2ccc(C#N)cc2)nnc(N2CCC(N(C)C(=O)c3cccnc3C(F)(F)F)CC2)c1C ; Cl ; Cl]

Combine 4-(4,5-dimethyl-6-(4-(methylamino)piperidin-1-yl)pyridazin-3-yl)benzonitrile (102 mg, 0.32 mmol), 2-(trifluoromethyl)nicotinic acid (70 mg, 0.38 mmol), and triethylamine (0.13 mL, 0.96 mmol) in DMF (10 mL). Add PyBOP (200 mg, 0.38 mmol) to the mixture and stir overnight at ambient temperature. Add $CH_2Cl_2$ to the reaction mixture and wash with brine. Dry the organic phase over $Na_2SO_4$, filter, and concentrate under reduced pressure. Purify the resulting residue by flash silica gel chromatography (20:5:1 hexanes: EtOAc:2 M $NH_3$/MeOH). Add excess 1 M HCl in $Et_2O$ to a solution of the free base in $CH_2Cl_2$/MeOH, and evaporate the solvents under $N_2$ gas to yield the title compound (103 mg, 57%). ES/MS m/z 495.2 (M+1).

Alternate Coupling Procedure:

Combine 4-(4,5-dimethyl-6-(4-(methylamino)piperidin-1-yl)pyridazin-3-yl)benzonitrile (300 mg, 0.93 mmol), 2-(trifluoromethyl)nicotinic acid (210 mg, 1.12 mmol) and diisopropylethylamine (0.79 mL, 4.51 mmol) in a 4:1 mixture of DMF and DMSO (20 mL). Heat the mixture briefly at 60° C. to dissolve the solids, and then cool to 0° C. Add a solution of perfluorophenyl diphenylphosphinate (750 mg, 1.96 mmol) in a 4:1 mixture of DMF and DMSO (1 mL) dropwise. Heat the resulting mixture at 60° C. overnight. Partition the reaction mixture between aqueous $NaHCO_3$ solution and $CH_2Cl_2$. Wash the organic layer with brine, dry over $Na_2SO_4$, filter, and concentrate under reduced pressure. Purify the resulting residue by flash silica gel chromatography (20:5:1 hexanes: EtOAc:2 M $NH_3$/MeOH) to provide the free base of the title compound (346 mg, 75%). ES/MS m/z 495.2 (M+1). Form the HCl salt as described above.

Prepare the piperidinyl amides in the table below by essentially following the procedure described in the first procedure for Example 14, using the appropriate dimethyl pyridazine and carboxylic acid. For Example 28, use 1.1 equivalents of 1 M HCl in MeOH (preform by dripping acetyl chloride into MeOH) then concentrate to provide the monohydrochloride salt. For Example 28, follow the alternate procedure of Example 14.

| Ex. No. | Chemical Name | Structure | ES/MS m/z |
|---|---|---|---|
| 15 | N-(1-(4,5-Dimethyl-6-phenylpyridazin-3-yl)piperidin-4-yl)-N-methyl-2-morpholino-4-(trifluoromethyl)thiazole-5-carboxamide hydrochloride | 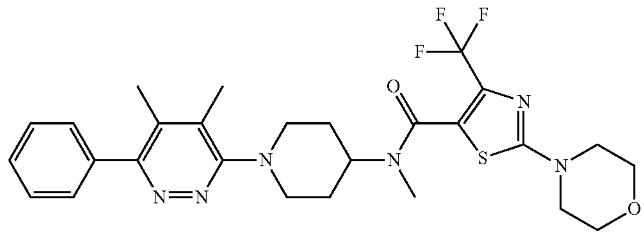 | 560.8 (M + 1) |
| 16 | N-(1-(6-(4-Fluorophenyl)-4,5-dimethylpyridazin-3-yl)piperidin-4-yl)-N-methyl-2-morpholino-4-(trifluoromethyl)thiazole-5-carboxamide hydrochloride | 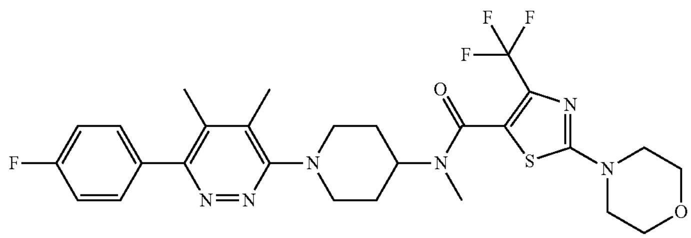 | 578.8 (M + 1) |
| 17 | 2-(Dimethylamino)-N-(1-(6-(4-fluorophenyl)-4,5-dimethylpyridazin-3-yl)piperidin-4-yl)-N-methyl-4-(trifluoromethyl)thiazole-5-carboxamide hydrochloride | 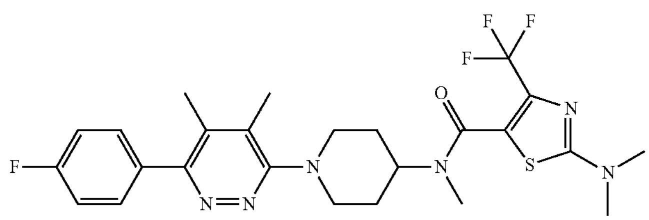 | 537.2 (M + 1) |
| 18 | N-(1-(4,5-Dimethyl-6-phenylpyridazin-3-yl)piperidin-4-yl)-2-(dimethylamino)-N-methyl-4-(trifluoromethyl)thiazole-5-carboxamide hydrochloride | 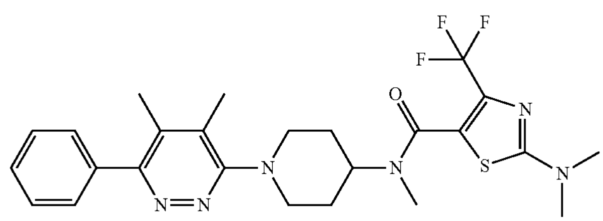 | 518.8 (M + 1) |
| 19 | 2-Amino-N-(1-(6-(4-Fluorophenyl)-4,5-dimethylpyridazin-3-yl)piperidin-4-yl)-N-methyl-4-(trifluoromethyl)thiazole-5-carboxamide hydrochloride | 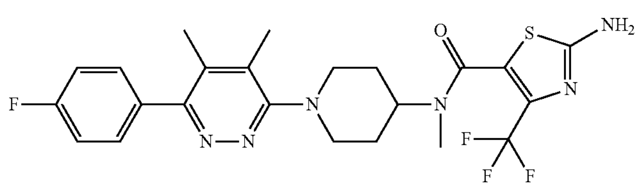 | 509.0 (M + 1) |
| 20 | 2-Amino-N-(1-(4,5-dimethyl-6-phenylpyridazin-3-yl)piperidin-4-yl)-N-methyl-4-(trifluoromethyl)thiazole-5-carboxamide hydrochloride | 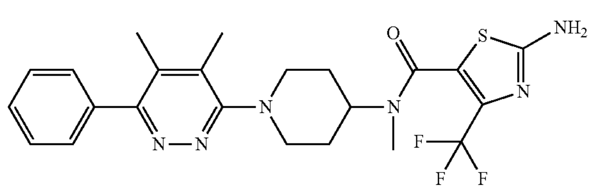 | 491.0 (M + 1) |

-continued

| Ex. No. | Chemical Name | Structure | ES/MS m/z |
|---|---|---|---|
| 21 | N-(1-(6-(4-Fluorophenyl)-4,5-dimethylpyridazin-3-yl)piperidin-4-yl)-N-methyl-2-(pyrrolidin-1-yl)-4-(trifluoromethyl)thiazole-5-carboxamide dihydrochloride | 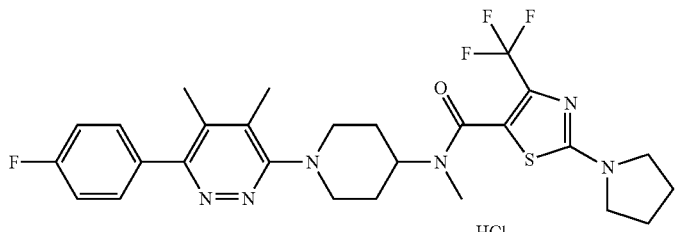 | 563.2 (M + 1) |
| 22 | N-(1-(6-(4-Fluorophenyl)-4,5-dimethylpyridazin-3-yl)piperidin-4-yl)-N-methyl-2-(trifluoromethyl)nicotinamide dihydrochloride | 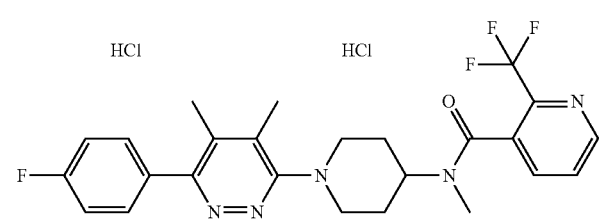 [SMILES: Cc1c(-c2ccc(F)cc2)nnc(N2CCC(N(C)C(=O)c3cccnc3C(F)(F)F)CC2)c1C ; Cl ; Cl] | 488.2 (M + 1) |
| 23 | N-(1-(4,5-Dimethyl-6-phenylpyridazin-3-yl)piperidin-4-yl)-N-methyl-2-(trifluoromethyl)nicotinamide dihydrochloride | 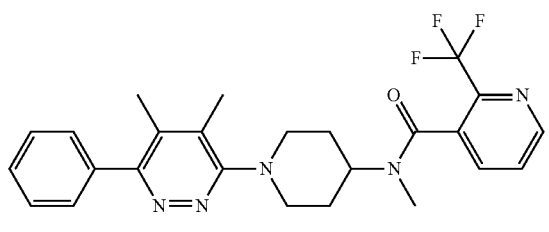 | 470.2 (M + 1) |
| 24 | N-(1-(6-(4-Fluorophenyl)-4,5-dimethylpyridazin-3-yl)piperidin-4-yl)-N-methyl-4-(trifluoromethyl)nicotinamide dihydrochloride | 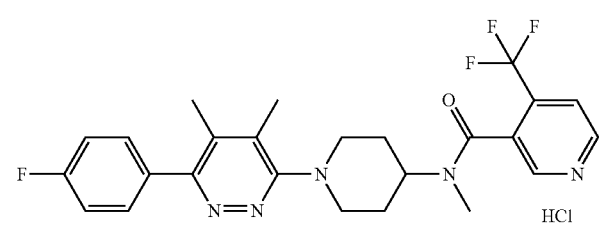 | 488.2 (M + 1) |
| 25 | N-(1-(6-(4-Fluorophenyl)-4,5-dimethylpyridazin-3-yl)piperidin-4-yl)-N,2-dimethyl-6-(trifluoromethyl)nicotinamide dihydrochloride | 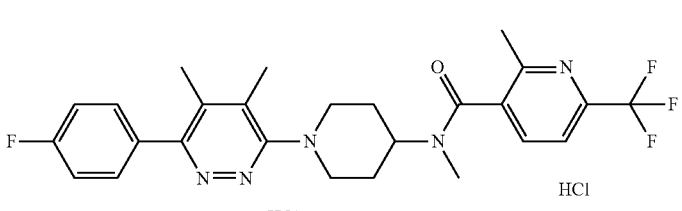 | 502.2 (M + 1) |
| 26 | 2-Chloro-N-(1-(6-(4-fluorophenyl)-4,5-dimethylpyridazin-3-yl)piperidin-4-yl)-N-methyl-4-(methylsulfonyl)benzamide hydrochloride | 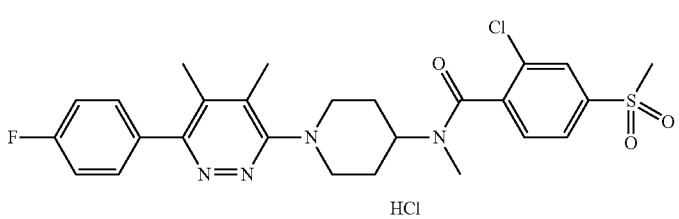 [SMILES: Cc1c(-c2ccc(F)cc2)nnc(N2CCC(N(C)C(=O)c3ccc(S(C)(=O)=O)cc3Cl)CC2)c1C ; Cl] | 531.2 (M + 1) |

-continued

| Ex. No. | Chemical Name | Structure | ES/MS m/z |
|---|---|---|---|
| 27 | N-(1-(4,5-Dimethyl-6-(pyridin-4-yl)pyridazin-3-yl)piperidin-4-yl)-N,1-dimethyl-3-(trifluoromethyl)-1H-pyrazole-4-carboxamide hydrochloride | 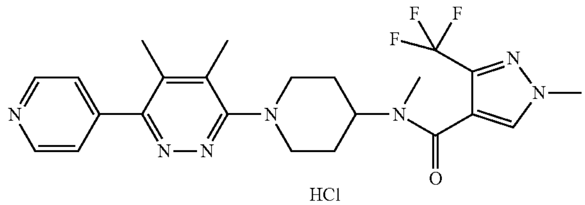 [SMILES: Cc1c(-c2ccncc2)nnc(N2CCC(N(C)C(=O)c3cn(C)nc3C(F)(F)F)CC2)c1C ; Cl] | 474.2 (M + 1) |
| 28 | 2-Amino-N-(1-(6-(4-cyanophenyl)-4,5-dimethylpyridazin-3-yl)piperidin-4-yl)-N-methyl-4-(trifluoromethyl)thiazole-5-carboxamide hydrochloride | 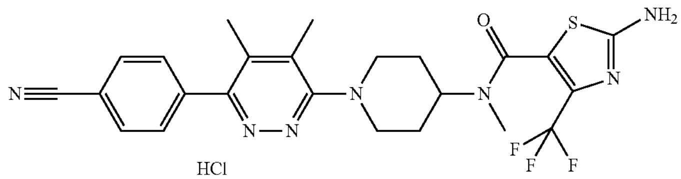 [SMILES: Cc1c(-c2ccc(C#N)cc2)nnc(N2CCC(N(C)C(=O)c3sc(N)nc3C(F)(F)F)CC2)c1C ; Cl] | 516.2 (M + 1) |

EXAMPLE 29

N-(1-(6-(4-Cyanophenyl)-4,5-dimethylpyridazin-3-yl)piperidin-4-yl)-N-methyl-4-(trifluoromethyl)nicotinamide hydrochloride

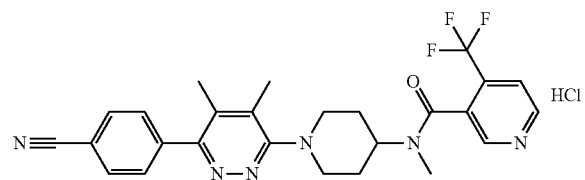 [SMILES: Cc1c(-c2ccc(C#N)cc2)nnc(N2CCC(N(C)C(=O)c3cnccc3C(F)(F)F)CC2)c1C ; Cl]

Treat a solution of 4-(4,5-dimethyl-6-(4-(methylamino)piperidin-1-yl)pyridazin-3-yl)benzonitrile (102 mg, 0.32 mmol), 4-(trifluoromethyl)nicotinic acid (81 mg, 0.42 mmol), triethylamine (0.07 mL, 0.5 mmol) in CH$_2$Cl$_2$ (4 mL) with EDCI (99 mg, 0.52 mmol) and stir for 3 d. Pour the reaction mixture into H$_2$O and extract with EtOAc. Wash the organic layer with H$_2$O, dry over Na$_2$SO$_4$, filter, and concentrate under reduced pressure. Purify by flash silica gel chromatography (gradient of 0 to 10% MeOH in CH$_2$Cl$_2$). Dissolve the free base in MeOH (2 mL) and add 1 M HCl in Et$_2$O (0.5 mL). Concentrate to provide the title compound (82 mg, 49%). ES/MS m/z 495.2 (M+1).

Prepare the piperidinyl amides in the table below by essentially following the procedure described in Example 29, using the appropriate carboxylic acid. For Examples 31-33, stir overnight. To form the HCl salts in Examples 31-33, dissolve the corresponding free base in MeOH and add 1.1 equivalents of methanolic HCl (preform by dripping acetyl chloride into MeOH) then concentrate.

| Ex. No. | Chemical Name | Structure | ES/MS m/z |
|---|---|---|---|
| 30 | N-(1-(4,5-Dimethyl-6-phenylpyridazin-3-yl)piperidin-4-yl)-N-methyl-4-(trifluoromethyl)nicotinamide hydrochloride | 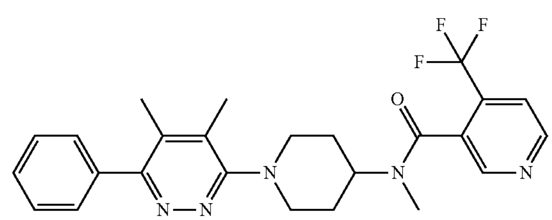 | 470.2 (M + 1) |
| 31 | 4,4-Difluoro-N-(1-(6-(4-fluorophenyl)-4,5-dimethylpyridazin-3-yl)piperidin-4-yl)-N-methylcyclohexanecarboxamide hydrochloride | 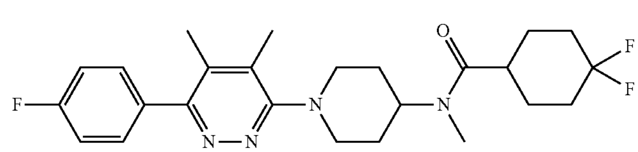 | 461.2 (M + 1) |

-continued

| Ex. No. | Chemical Name | Structure | ES/MS m/z |
|---|---|---|---|
| 32 | N-(1-(6-(4-Cyanophenyl)-4,5-dimethylpyridazin-3-yl)piperidin-4-yl)-4,4-difluoro-N-methylcyclohexanecarboxamide hydrochloride | 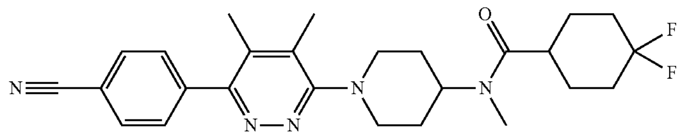 | 468.2 (M + 1) |
| 33 | N-(1-(4,5-Dimethyl-6-phenylpyridazin-3-yl)piperidin-4-yl)-4,4-difluoro-N-methylcyclohexanecarboxamide hydrochloride | 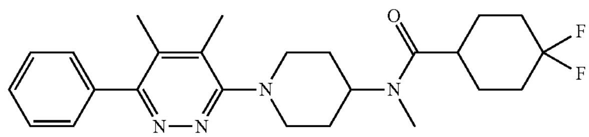 | 443.2 (M + 1) |

EXAMPLE 34

(S)-N-(1-(6-(4-Fluorophenyl)-4,5-dimethylpyridazin-3-yl)piperidin-4-yl)-N-methylpiperidine-2-carboxamide dihydrochloride

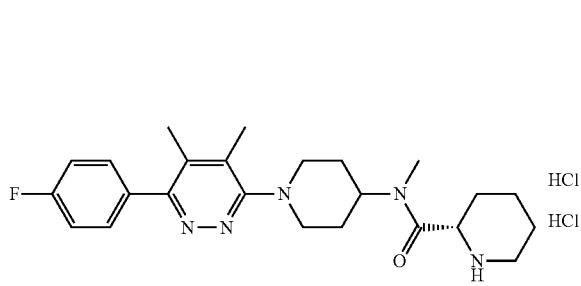 [SMILES: Cc1c(-c2ccc(F)cc2)nnc(N2CCC(N(C)C(=O)[C@@H]3CCCCN3)CC2)c1C ; Cl ; Cl]

Add 4 M HCl in 1,4-dioxane (1.00 mL, 4.00 mmol) to a solution of (S)-tert-butyl 2-((1-(6-(4-fluorophenyl)-4,5-dimethylpyridazin-3-yl)piperidin-4-yl)(methyl)carbamoyl)piperidine-1-carboxylate (80 mg, 0.152 mmol) in $CH_2Cl_2$ (2 mL). Stir the resulting mixture for 4 h at ambient temperature. Concentrate under reduced pressure and dry the residue in a vacuum oven at 45° C. to provide the title compound as pale yellow foam (79 mg, quantitative). ES/MS m/z 426.2 (M+1).

EXAMPLE 35

N-(1-(6-(4-Fluorophenyl)-4,5-dimethylpyridazin-3-yl)piperidin-4-yl)-N,1-dimethyl-5-(trifluoromethyl)-1H-pyrazole-4-carboxamide dihydrochloride

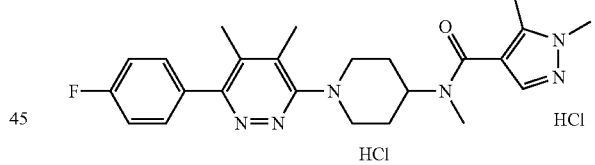

Dissolve 1-(6-(4-fluorophenyl)-4,5-dimethylpyridazin-3-yl)-N-methylpiperidin-4-amine (800 mg, 4.12 mmol) in DMF (25 mL). Add 1-methyl-5-(trifluoromethyl)-1H-pyrazole-4-carboxylic acid (1.08 g, 3.44 mmol), triethylamine (1.44 mL, 10.3 mmol) and PyBOP (2.68 g, 5.15 mmol). Stir at ambient temperature for 3 h. Concentrate the reaction mixture and purify the residue by flash silica gel chromatography using a gradient of 0-100% (5:1 EtOAc:2 M $NH_3$/MeOH) in hexanes. Dissolve the isolated product in $CH_2Cl_2$ (10 mL) and add 2 M HCl in $Et_2O$ (8 mL). Remove solvents under a stream of $N_2$ and dry in a vacuum oven at 50° C. overnight to afford the title compound (612 mg, 32%). ES/MS (m/z) 491.2 (M+1).

Prepare the amides in the table below by essentially following the procedure described in Example 34, using the appropriate carboxylic acid. Purify Example 36 over an SCX column (eluting with 2 M $NH_3$/MeOH) followed by flash chromatography.

| Ex. No. | Chemical Name | Structure | ES/MS m/z |
|---|---|---|---|
| 36 | N-(1-(6-(4-Fluorophenyl)-4,5-dimethylpyridazin-3-yl)piperidin-4-yl)-N,1-dimethyl-3-(trifluoromethyl)-1H-pyrazole-4-carboxamide dihydrochloride | 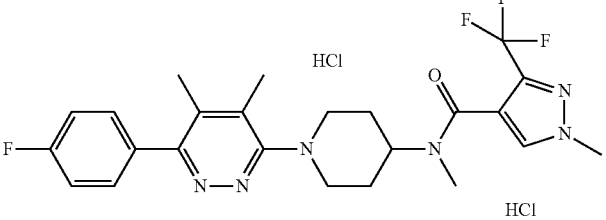 | 491.2 (M + 1) |
| 37 | N-(1-(6-(4-Fluorophenyl)-4,5-dimethylpyridazin-3-yl)piperidin-4-yl)-N,1-dimethyl-5-(methylsulfonyl)-1H-pyrazole-4-carboxamide hydrochloride | 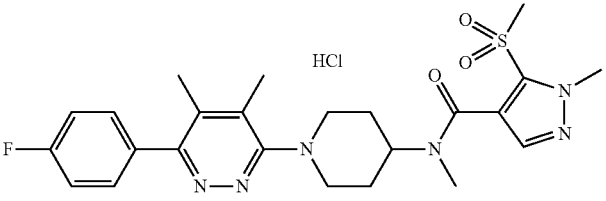 [SMILES: Cc1c(-c2ccc(F)cc2)nnc(N2CCC(N(C)C(=O)c3cnn(C)c3S(C)(=O)=O)CC2)c1C ; Cl] | 501.0 (M + 1) |

EXAMPLE 38

N-(1-(6-(4-Fluorophenyl)-4,5-dimethylpyridazin-3-yl)piperidin-4-yl)-N-methyl-3-(trifluoromethyl)-1H-pyrazole-4-carboxamide dihydrochloride

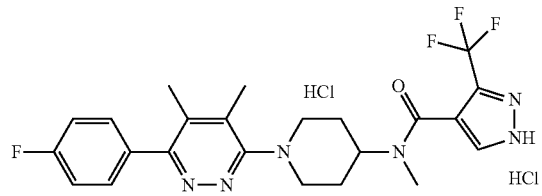 [SMILES: Cc1c(-c2ccc(F)cc2)nnc(N2CCC(N(C)C(=O)c3c[nH]nc3C(F)(F)F)CC2)c1C ; Cl ; Cl]

Add trifluoroacetic acid (10 mL) to N-(1-(6-(4-fluorophenyl)-4,5-dimethylpyridazin-3-yl)piperidin-4-yl)-1-(4-methoxybenzyl)-N-methyl-3-(trifluoromethyl)-1H-pyrazole-4-carboxamide (99 mg, 0.12 mmol) and heat at reflux under $N_2$ overnight. Concentrate under reduced pressure. Dissolve the residue in 20% iPrOH in $CHCl_3$, and wash with saturated aqueous $Na_2CO_3$ solution. Extract the aqueous layer with 20% iPrOH in $CHCl_3$. Combine the organic layers, dry over $MgSO_4$, filter, and concentrate under reduced pressure. Purify the residue by flash silica gel chromatography (gradient of 0 to 10% 2 M $NH_3$/MeOH in $CH_2Cl_2$). Dissolve the purified free base in $CH_2Cl_2$ (2 mL) and add 1 M HCl in $Et_2O$ (0.5 mL) dropwise. Stir for 30 min. Concentrate and dry in a vacuum oven at 50° C. overnight to provide the title compound (55 mg, 60%). ES/MS m/z 477.0 (M+1).

Biology

Hedgehog has been implicated as a survival factor for the following cancers: basal cell carcinoma; upper gastro intestinal tract cancers (esophagus, stomach, pancreas, and biliary tract); prostate cancer; breast cancer; small cell lung cancer; non-small cell lung cancer; B-cell lymphoma; multiple myeloma; gastric cancer; ovarian cancer; colorectal cancer; liver cancer; melanoma; kidney cancer; and brain cancer.

Elements of the hedgehog pathway have been asserted to be potential drug targets for the treatment of cancers. A Daoy cell line established from medulloblastoma tumor (ATCC, HTB-186), is responsive to Hh ligands. When these cells are treated with exogenously added Shh-conditioned media, Hh signaling pathway is activated and results in an increased expression of Gli1. Cyclopamine, an alkaloid isolated from the corn lily *Veratrum californicum* is a weak hedgehog antagonist and has been shown to suppress the expression of Gli1 in response to Shh stimulation. Recent observations suggest that cyclopamine inhibits the growth of cultured medulloblastoma cells and allografts. Using this Daoy cell model system, potent inhibitors of hedgehog signaling pathways can be identified. Since the compounds of the present invention are hedgehog antagonists, they are suitable for treating the aforementioned tumor types.

Determination of Biological Activity $IC_{50}$

The following assay protocol and results thereof further demonstrate the utility and efficacy of the compounds and methods of the current invention. Functional assays provide support that the compounds of the present invention exhibit the ability to inhibit Shh signaling. All ligands, solvents, and reagents employed in the following assay are readily available from commercial sources or can be readily prepared by one skilled in the art.

Biological activity is determined using a functional assay in Daoy neuronal cancer cells and measures levels of Gli1 ribonucleic acid via a bDNA (branched deoxyribonucleic acid) assay system (Panomics, Inc., Fremont, Calif.). Gli was originally discovered in a Glioblastoma cell line and encodes a zinc finger protein that is activated by Shh signaling. The maximum response is obtained by inducing Gli1 transcription in the Daoy cells with conditioned medium (human embryonic kidney, HEK-293 cells stably expressing recombinant Shh) for 24 hours and then measuring the amount of stimulated Gli1 transcript. The minimum response is the amount of Gli1 transcript inhibited with a control compound in Daoy cells that have been stimulated with conditioned media (human embryonic kidney, HEK-293 cells stably expressing recombinant Shh) for 24 hours.

Functional Assay for Measuring the Inhibition of Gli1 in Daoy Cells

The bDNA assay system utilizes the technology of branched-chain DNA to allow amplification of a target ribonucleic acid (transcript). The technology employs three types of synthetic hybrid short Gli1-specific cDNA probes that determine the specificity of the target transcript [capture extenders (CEs), label extenders (LEs), and blockers (BLs)] that hybridize as a complex with the target transcripts to amplify the hybridization signal. The addition of a chemilumigenic substrate during the amplification step allows for detection using luminescence.

The Daoy cell line obtained from American Type Culture collection (ATCC) is a Shh-responsive human neuronal tumor cell line and was established in 1985 from a desmoplastic cerebellar medullablastoma tumor, a physiologically relevant tumor cell line. Endogenous levels of Gli1 transcripts levels are low in Daoy cells but can be stimulated by using conditioned media taken from cells stably over-expressing human Shh (a HEK-293 cell line stably transfected with hShh).

Daoy cells are grown to confluency in tissue culture T225-flasks in Daoy growth media containing Minimum Essential Medium (MEM) plus 10% Fetal Bovine Serum (FBS) with 0.1 nM non-essential amino acids and 1 mM sodium pyruvate. The cells are removed from the T225-flasks using trypsin ethylenediaminetetraacetic acid (EDTA), centrifuged, resuspended in media, and then counted.

The Daoy cells are then seeded at 50,000 cells per well in growth media in Costar 96 well clear tissue culture plates and allowed to incubate overnight at 37° C. under 5% carbon dioxide ($CO_2$). The cells are washed one time in phosphate buffered saline (PBS) followed by addition of 100 µL of Shh Conditioned Media (Shh-CM) to stimulate levels of Gli1 expression. Shh-CM is diluted to achieve maximum stimulation using control growth media—0.1% FBS/DMEM (Dulbeccos Modified Eagle Medium). Daoy cells treated with Shh-CM are then treated with various concentrations of hedgehog inhibitors ranging from approximately 1 µM to 0.1 nM. Test compounds are allowed to incubate for 24 hours at 37° C. under 5% $CO_2$.

The measurement of the Gli1 transcript is performed by using the Quantigene 2.0 Gli1 assay as described by the manufacturer (Panomics, Inc.). Prepare a diluted lysis mixture (DLM) buffer, which includes Proteinase K. After a 24 hour incubation with compound, the cells are washed one time with PBS and 180 µL of DLM is added to the cells. The cell plate containing the lysis buffer is sealed and placed at 55° C. for 30 to 45 minutes. The resulting cell lysates are then triturated 5 times. A working probe set containing Gli1 probes is made by diluting the probes in the DLM according to the manufacturer's directions, and then 20 µL of the working probe set is added to the bDNA assay plates along with 80 µL of the Daoy lysates. The plates are sealed and incubated overnight at 55° C. The bDNA plates are then processed according to the manufacturer's directions. The signal is quantified by reading the plates on a Perkin Elmer Envision reader detecting luminescence. The luminescent signal is directly proportional to the amount of target transcript present in the sample.

The luminescent signal data from the functional assay are used to calculate the $IC_{50}$ for the in vitro assay. The data are calculated based on the maximum control values (Daoy cells treated with Shh-CM) and the minimum control value (Daoy cells treated with Shh-CM and an inhibitory concentration of a control compound, 1 µM of N-(3-(1H-benzo[d]imidazol-2-yl)-4-chlorophenyl)-3,5-dimethoxybenzamide). A four parameter logistic curve fit is used to generate the $IC_{50}$ values using ActivityBase software programs version 5.3, equation 205 (*Assay Guidance Manual Version* 5.0, 2008, Eli Lilly and Company and NIH Chemical Genomics Center).

Following the protocol described, the compounds of the invention exemplified herein display an $IC_{50}$ of <15 nM. For example, the compound of Example 14 has an $IC_{50}$ of approximately 1.27 nM with a standard error of 0.114 (n=4) and the compound of Example 34 has an $IC_{50}$ of approximately 1.22 nM with a standard error 0.293 (n=3) in the assay described above. These results provide evidence that the compounds of the present invention are hedgehog antagonists and, as such, are useful as anticancer agents.

We claim:

1. A compound of the following formula:

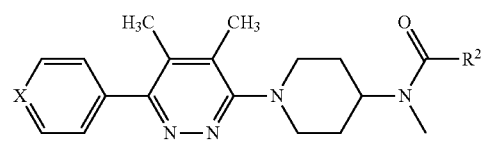

or a pharmaceutically acceptable salt thereof, wherein:

X is C—$R^1$ or N;

$R^1$ is hydrogen, fluoro or cyano;

$R^2$ is

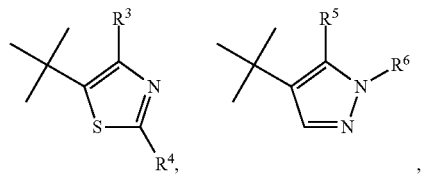

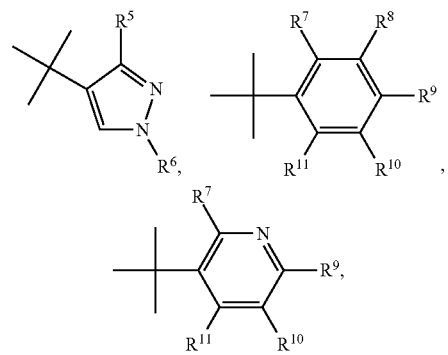

piperidinyl, or gem di-F-substituted cyclohexyl;

$R^3$ is methyl or trifluoromethyl;

$R^4$ is pyrrolidinyl, morpholinyl, pyridyl, amino or dimethylamino;

$R^5$ is trifluoromethyl or methylsulfonyl;

$R^6$ is hydrogen or methyl; and $R^7$, $R^8$, $R^9$, $R^{10}$ and $R^{11}$ are independently hydrogen fluoro, cyano, chloro, methyl, trifluoromethyl, trifluoromethoxy or methylsulfonyl, provided that at least two of $R^7$, $R^8$, $R^9$, $R^{10}$ and $R^{11}$ are hydrogen.

2. The compound of claim 1 wherein X is C—$R^1$, or a pharmaceutically acceptable salt thereof.

3. The compound of claim 1 wherein $R^2$ is:

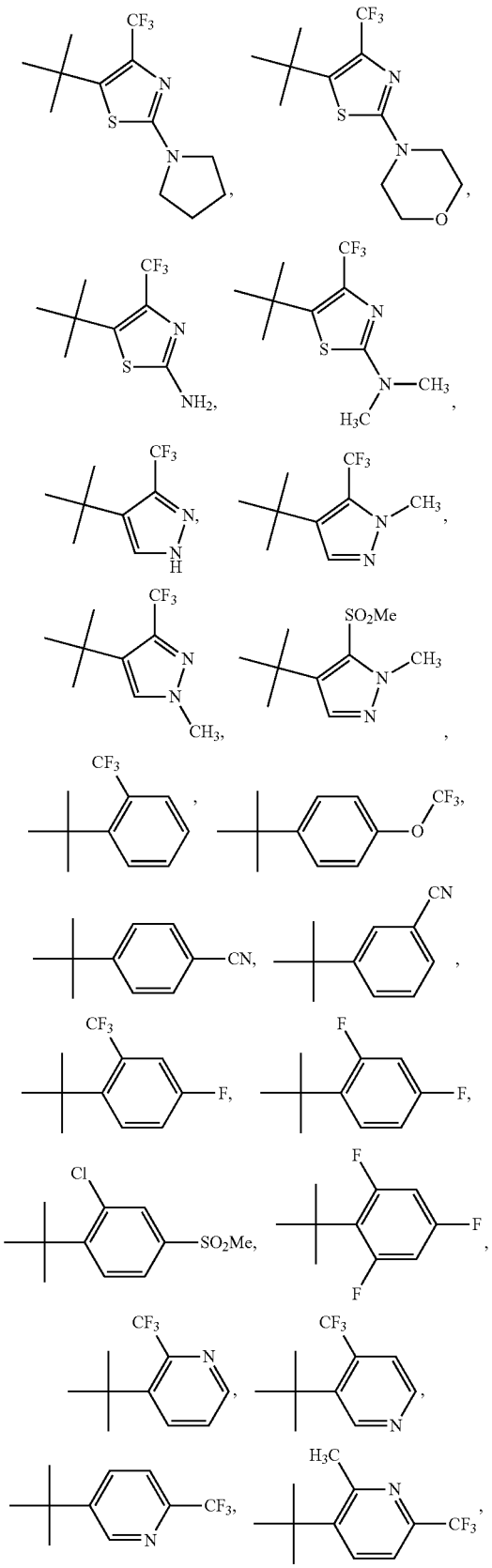

or a pharmaceutically acceptable salt thereof.

4. The compound of claim 3 wherein X is C—$R^1$, or a pharmaceutically acceptable salt thereof.

5. The compound of claim 2 wherein $R^2$ is or a pharmaceutically acceptable salt thereof.

6. The compound of claim 5 wherein $R^5$ is trifluoromethyl and $R^6$ is methyl, or a pharmaceutically acceptable salt thereof.

7. The compound of claim 2 wherein $R^2$ is or a pharmaceutically acceptable salt thereof.

8. The compound of claim 7 wherein $R^7$ is trifluoromethyl and $R^9$, $R^{10}$, and $R^{11}$ are hydrogen, or a pharmaceutically acceptable salt thereof.

9. A pharmaceutical composition comprising a compound of claim 1, or a pharmaceutically acceptable salt thereof, in combination with a pharmaceutically acceptable carrier, diluent or excipient.

10. A compound of claim 4 which is:
N-(1-(6-(4-cyanophenyl)-4,5-dimethylpyridazin-3-yl)piperidin-4-yl)-N-methyl-2-(trifluoromethyl)nicotinamide,
N-(1-(6-(4-fluorophenyl)-4,5-dimethylpyridazin-3-yl)piperidin-4-yl)-N-methyl-2-(trifluoromethyl)nicotinamide,
N-(1-(4,5-dimethyl-6-phenylpyridazin-3-yl)piperidin-4-yl)-N-methyl-2-(trifluoromethyl)nicotinamide,
N-(1-(6-(4-fluorophenyl)-4,5-dimethylpyridazin-3-yl)piperidin-4-yl)-N-methyl-4-(trifluoromethyl)nicotinamide,
N-(1-(6-(4-cyanophenyl)-4,5-dimethylpyridazin-3-yl)piperidin-4-yl)-N-methyl-4-(trifluoromethyl)nicotinamide,
N-(1-(4,5-dimethyl-6-phenylpyridazin-3-yl)piperidin-4-yl)-N-methyl-4-(trifluoromethyl)nicotinamide, or
N-(1-(6-(4-fluorophenyl)-4,5-dimethylpyridazin-3-yl)piperidin-4-yl)-N,1-dimethyl-5-(trifluoromethyl)-1H-pyrazole-4-carboxamide,
or a pharmaceutically acceptable salt thereof.

11. A compound of claim 10 which is N-(1-(6-(4-cyanophenyl)-4,5-dimethylpyridazin-3-yl)piperidin-4-yl)-N-methyl-2-(trifluoromethyl)nicotinamide, or a pharmaceutically acceptable salt thereof.

12. The compound of claim 11 which is N-(1-(6-(4-cyanophenyl)-4,5-dimethylpyridazin-3-yl)piperidin-4-yl)-N-methyl-2-(trifluoromethyl)nicotinamide dihydrochloride.

13. A compound of claim 10 which is:
- N-(1-(6-(4-fluorophenyl)-4,5-dimethylpyridazin-3-yl)piperidin-4-yl)-N-methyl-2-(trifluoromethyl)nicotinamide dihydrochloride,
- N-(1-(4,5-dimethyl-6-phenylpyridazin-3-yl)piperidin-4-yl)-N-methyl-2-(trifluoromethyl)nicotinamide dihydrochloride,
- N-(1-(6-(4-fluorophenyl)-4,5-dimethylpyridazin-3-yl)piperidin-4-yl)-N-methyl-4-(trifluoromethyl)nicotinamide dihydrochloride,
- N-(1-(6-(4-cyanophenyl)-4,5-dimethylpyridazin-3-yl)piperidin-4-yl)-N-methyl-4-(trifluoromethyl)nicotinamide hydrochloride,
- N-(1-(4,5-dimethyl-6-phenylpyridazin-3-yl)piperidin-4-yl)-N-methyl-4-(trifluoromethyl)nicotinamide hydrochloride, or
- N-(1-(6-(4-fluorophenyl)-4,5-dimethylpyridazin-3-yl)piperidin-4-yl)-N,1-dimethyl-5-(trifluoromethyl)-1H-pyrazole-4-carboxamide dihydrochloride.

14. A pharmaceutical composition comprising a compound of claim 10, or a pharmaceutically acceptable salt thereof, in combination with a pharmaceutically acceptable carrier, diluent or excipient.

15. A pharmaceutical composition comprising a compound of claim 11, or a pharmaceutically acceptable salt thereof, in combination with a pharmaceutically acceptable carrier, diluent or excipient.

* * * * *